US011400098B2

(12) United States Patent
Gallo et al.

(10) Patent No.: US 11,400,098 B2
(45) Date of Patent: *Aug. 2, 2022

(54) METHOD OF TREATING MICROBIAL INFECTIONS

(71) Applicant: The Regents of the University of California, Oakland, CA (US)

(72) Inventors: Richard L. Gallo, San Diego, CA (US); Teruaki Nakatsuji, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/724,005

(22) Filed: Dec. 20, 2019

(65) Prior Publication Data

US 2020/0281935 A1 Sep. 10, 2020

Related U.S. Application Data

(60) Continuation of application No. 16/141,740, filed on Sep. 25, 2018, now abandoned, and application No.
(Continued)

(51) Int. Cl.
| | |
|---|---|
| *A61K 35/00* | (2006.01) |
| *A61K 31/5395* | (2006.01) |
| *A61K 31/5365* | (2006.01) |
| *C07D 413/04* | (2006.01) |
| *C07D 473/18* | (2006.01) |
| *C07D 473/34* | (2006.01) |
| *C07D 487/04* | (2006.01) |

(Continued)

(52) U.S. Cl.
CPC ........ *A61K 31/5395* (2013.01); *A61K 9/0014* (2013.01); *A61K 31/4188* (2013.01); *A61K 31/506* (2013.01); *A61K 31/5025* (2013.01); *A61K 31/519* (2013.01); *A61K 31/52* (2013.01); *A61K 31/53* (2013.01); *A61K 31/5365* (2013.01); *A61K 35/74* (2013.01); *A61K 45/06* (2013.01); *C07D 413/04* (2013.01); *C07D 473/18* (2013.01); *C07D 473/34* (2013.01); *C07D 487/04* (2013.01); *C07D 498/04* (2013.01); *A61P 31/04* (2018.01); *Y02A 50/30* (2018.01)

(58) Field of Classification Search
CPC ..................................................... A61K 35/74
USPC ........................................ 424/780; 514/263.4
See application file for complete search history.

(56) References Cited

U.S. PATENT DOCUMENTS 10,085,997 B2 * 10/2018 Gallo .................. A61K 31/506
2007/0105848 A1 5/2007 Wood et al.

FOREIGN PATENT DOCUMENTS

WO 2007135380 A2 11/2007

OTHER PUBLICATIONS

Kim, Yong, International Search Report and Written Opinion, PCT/US2012/025044, Korean Intellectual Property Office, dated Feb. 28, 2013.
(Continued)

*Primary Examiner* — Shengjun Wang
(74) *Attorney, Agent, or Firm* — Gavrilovich, Dodd & Lindsey LLP

(57) ABSTRACT

The disclosure provides for novel antimicrobial agents, methods of making, and methods of use thereof.

22 Claims, 17 Drawing Sheets

Related U.S. Application Data

16/724,005, which is a continuation of application No. 15/483,101, filed on Apr. 10, 2017, now Pat. No. 10,085,997, which is a continuation of application No. 14/750,979, filed on Jun. 25, 2015, now abandoned, which is a division of application No. 13/985,548, filed as application No. PCT/US2012/025044 on Feb. 14, 2012, now abandoned.

(60) Provisional application No. 61/482,590, filed on May 4, 2011, provisional application No. 61/443,149, filed on Feb. 15, 2011.

(51) Int. Cl.
| | | |
|---|---|---|
| *C07D 498/04* | (2006.01) | |
| *A61K 45/06* | (2006.01) | |
| *A61K 31/4188* | (2006.01) | |
| *A61K 31/5025* | (2006.01) | |
| *A61K 31/506* | (2006.01) | |
| *A61K 31/52* | (2006.01) | |
| *A61K 31/53* | (2006.01) | |
| *A61K 9/00* | (2006.01) | |
| *A61K 31/519* | (2006.01) | |
| *A61K 35/74* | (2015.01) | |
| *A61P 31/04* | (2006.01) | |

(56) References Cited

OTHER PUBLICATIONS

Nickitas-Etienne, Athina, International Preliminary Report on Patentabilityt and Written Opinion, PCT/US2012/025044, The International Bureau of WIPO, dated Aug. 21, 2013.

Sahl et al., "Production, purification and chemical properties of an antistaphylococcal agent produced by *Staphylococcus epidermidis*," J. General Microbiol., 1981, pp. 277-384, vol. 127.

Yuping et al., "Activation of TLR2 by a small molecule produced by *Staphylococcus epidermidis* increase antimicrobial defense against bacterial skin infections," J. Invest. Dermatology, 2010, pp. 2211-2221, vol. 130.

Nakatsuji, et al. "A commensal strain of *Staphylococcus epidermidis* protects against skin neoplasia." Science Advances 4.2 (2018): eaao4502.

\* cited by examiner

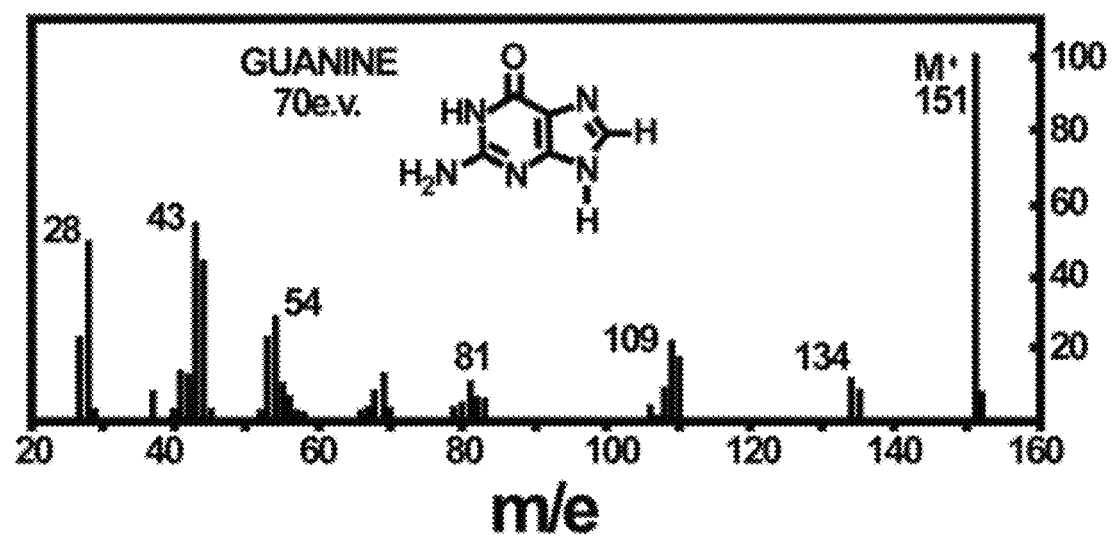
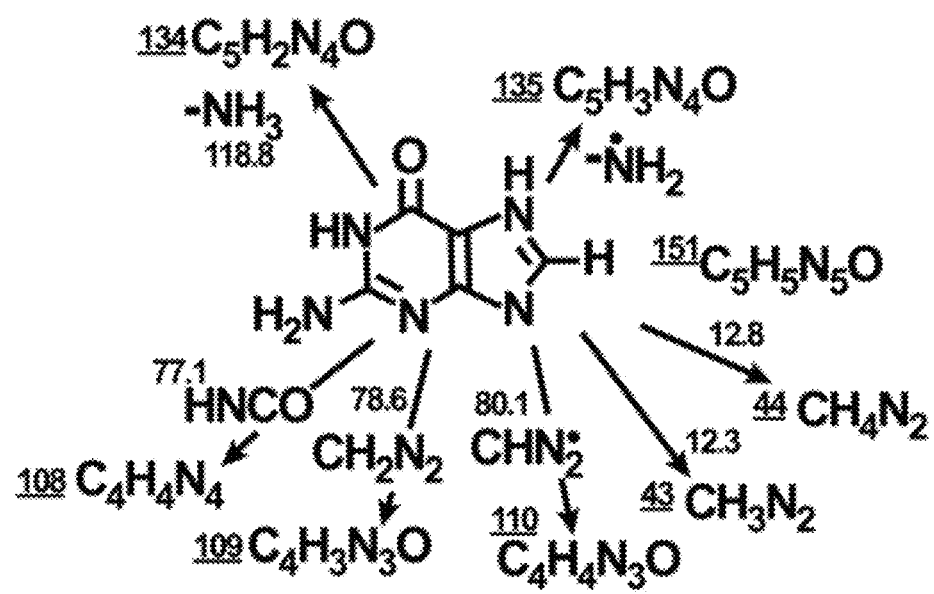
FIGURE 7

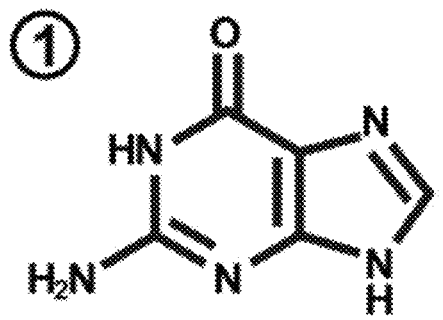
Guanine
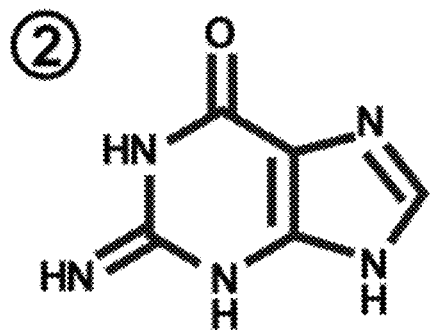
2-Imino-1,2,3,9-tetrahydro-purin-6-one
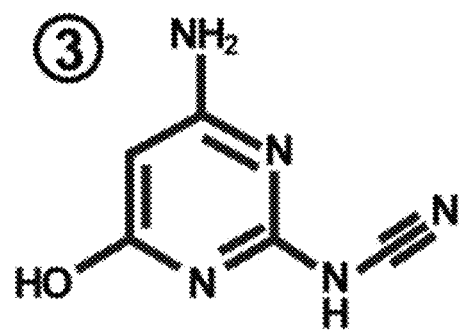
4-Amino-2-yl-cyanoamino-6-hydroxypyrimidine
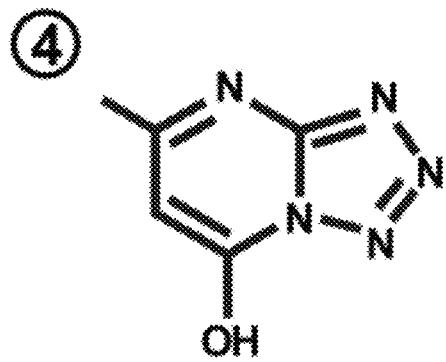
5-Hydroxy-7-methyl-1,2,3,8-tetraazaindolizine
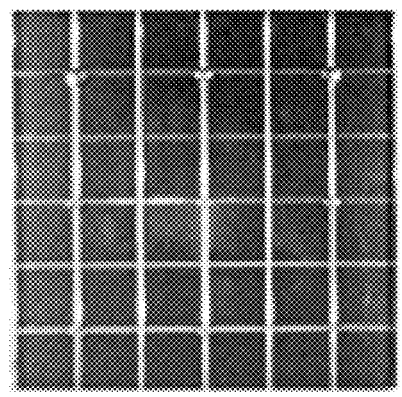
FIGURE 11

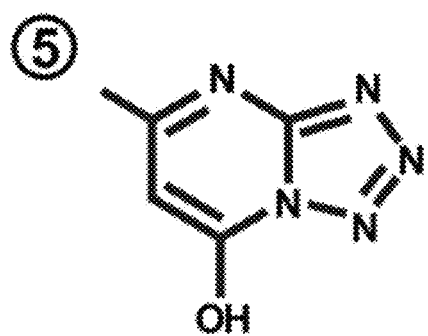
5-Methyl-tetrazolo (1,5-A)pyrimidin-7-ol
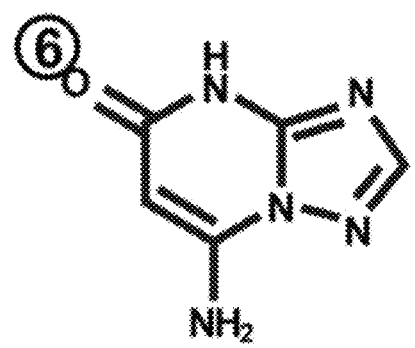
7-Amino-S-triazolo (1,5-A)pyrimidin-5(4H)-one
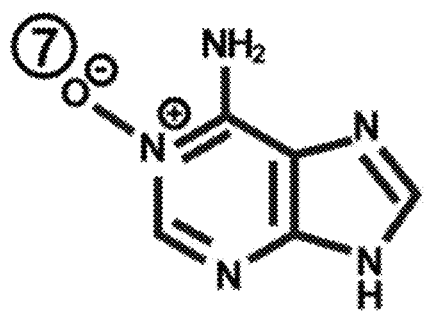
Adenine N1-oxide
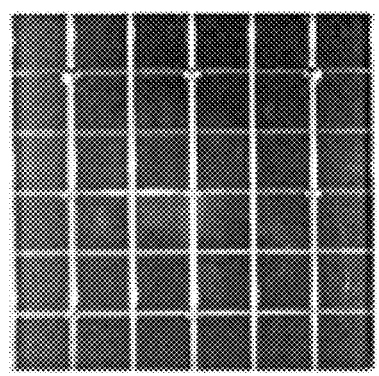
FIGURE 11 (cont'd)

METHOD OF TREATING MICROBIAL INFECTIONS

CROSS REFERENCE TO RELATED APPLICATIONS

This application is a continuation of U.S. application Ser. No. 16/141,740, filed Sep. 25, 2018, which is a continuation of U.S. application Ser. No. 15/483,101, filed Apr. 10, 2017, which is a continuation of U.S. application Ser. No. 14/750,979, filed Jun. 25, 2015, which is a divisional of U.S. patent application Ser. No. 13/985,548, filed Aug. 14, 2013, which is a U.S. National Stage application filed under 35 U.S.C. § 371 and claims priority to International Application No. PCT/US2012/025044, filed Feb. 14, 2012, which application claims priority under 35 U.S.C. § 119 from Provisional Application Ser. No. 61/443,149, filed Feb. 15, 2011 and from Provisional Application Ser. No. 61/482,590, filed May 4, 2011, the disclosures of which are incorporated herein by reference.

STATEMENT REGARDING FEDERALLY SPONSORED RESEARCH

This invention was made with Government support under Grant No. AI083358, awarded by the National Institutes of Health. The Government has certain rights in the invention.

TECHNICAL FIELD

The disclosure relates to anti-microbial agents, methods of making, and methods of use thereof.

BACKGROUND

Ogston (1881) coined the genus *Staphylococcus* to describe grapelike clusters of bacteria (staphylo=grape, Gr.) recovered in pus from surgical abscesses. Entering its seventh decade, the era of antimicrobial therapy has greatly reduced morbidity and mortality from infectious diseases. However, the emergence of resistant microorganisms has now reached epidemic proportions and poses great challenges to the medical community. Worrisome trends are particularly evident in the pre-eminent Gram-positive bacterial pathogen *S. aureus*, which has become increasingly unresponsive to first-line antibiotic therapies. *S. aureus* is probably the most common cause of life-threatening acute bacterial infections in the world, and is capable of causing a diverse array of diseases, ranging in severity from a simple boil or impetigo to fulminant sepsis or toxic shock syndrome. *S. aureus* is the single leading cause of bacteremia, hospital-related (nosocomial) infections, skin and soft tissue infections, wound infections, and bone and joint infections. It is one of the most common agents of endocarditis and food poisoning.

National prospective surveillance of over 24,000 invasive bacterial isolates show disease-associated *S. aureus* strains with methicillin resistance (MRSA) have increased from 22% in 1995 to 57% currently. MRSA are now frequently identified in community-acquired infections as well as in hospital settings. A half-century of synthesizing analogs based on <10 antibacterial scaffolds has resulted in the development and marketing of >100 antibacterial agents but, with the exception of the oxazolidinone core, no new scaffolds have emerged in the past 30 years to address the emerging resistance problems.

Classic antibiotic approaches attempt to kill or suppress growth of bacteria by targeting essential cell functions such as cell wall biosynthesis, protein synthesis, DNA replication, RNA polymerase, or metabolic pathways. These conventional therapies run a high risk of toxicity since many of these cell functions are also essential to mammalian cells and require fine molecular distinction between the microbial target and the host cell counterpart(s). Second, the repetitive use of the same targets means that when a bacterium evolves resistance to a particular antibiotic agent during therapy, it can become simultaneously cross resistant to other agents acting on the same target, even though the bacterium has never been exposed to the other agents. Third, conventional therapies exert a "life-or-death" challenge upon the bacterium, and thus a strong selective pressure to evolve resistance to the antimicrobial agent. Finally, many current antibiotics have very broad spectrums of activity, with the side effect of eradicating many components of the normal flora, leading to undesired complications such as *Clostridium difficile* colitis or secondary fungal infections (e.g. *Candida*).

The emergence of MRSA has compromised the clinical utility of methicillin and related antibiotics (oxacillin, dicloxacillin) and all cephalosporings (e.g. cefazolin, cephalexin) in empiric therapy of *S. aureus* infections. MRSA often have significant levels of resistance to macrolides (e.g. erythromycin), beta-lactamase inhibitor combinations (e.g. Unasyn, Augmentin) and fluoroquinolones (e.g. ciprofloxacin), and are occasionally resistant to clindamycin, trimethoprim/sulfamethoxisol (Bactrim), and rifampin. In serious *S. aureus* infection, intravenous vancomycin is the last resort, but there have now also been alarming reports of *S. aureus* resistance to vancomycin, an intravenous antibiotic commonly used to treat MRSA.

New anti-MRSA agents such as linezolid (Zyvox®) or quinupristin/dalfopristin (Synercid®), both of which utilize the traditional target of binding to the ribosomal subunits to inhibit RNA synthesis are prohibitively expensive.

Existing antibiotic therapies non-specifically kill the majority of skin-residing bacteria, disrupting the homeostasis of skin resident microflora. For example, benzoyl peroxide (BPO) is one of the most frequently used topical medications. BPO strongly suppresses the growth of *S. epidermidis*. *S. epidermidis* contributes to the skin resident microflora-based defense of the skin epithelium. The imbalance of microflora could contribute to the pathogenesis of skin inflammatory diseases, such as atopic dermatitis, rosacea and acne vulgaris etc.

STATEMENT REGARDING BIOLOGICAL DEPOSIT

Under the provisions of the Budapest Treaty on the International Recognition of the Deposit of Microorganism for the Purposes of Patent Procedure, *Staphylococcus epidermidis* MO34 was deposited on Mar. 22, 2018 with the American Type Culture Collection, 10801 University Boulevard, Manassas, Va. 20110-2209, as ATCC Number PTA-125025 (strain designation S.epi-MO34 UCSD 20180315). This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the

SUMMARY

The disclosure also provides a method of preparing and substantially purifying a "firmocidin", a compound of the disclosure. In one embodiment, the method comprises extracting a flow-through from a 3K cut-off of the media and performing organic extraction, followed by separating on an $NH_2$-100 column eluted with a linear gradient of water in acetonitrile for 25 min. In a more specific embodiment, the method comprises obtaining *S. epidermidis* culture media, collecting the flow-through of the media using a 3K cut-off membrane, lyophilizing the collected flow through, resuspending the lyophilized product in methanol and partitioning in 90% acetonitrile, collecting the organic phase, lyophilizing the organic phase, resuspending the lyophilized organic phase in an aqueous media, filtering on a $C_{18}$ sep-pak cartridge, lyophilizing and resuspending in methanol, collecting the supernatant, lyophilizing, partitioning in acetonitrile and collecting the supernatant, and separating on Taskgel $NH_2$-100 column eluted with a linear gradient of 5-20% water in acetonitrile for 25 min. The disclosure also provides a composition obtained by the foregoing method, wherein the composition has anti-microbial activity.

In a particular embodiment, the disclosure provides for a firmocidin compound selected from the group comprising:

(a) Formula I:

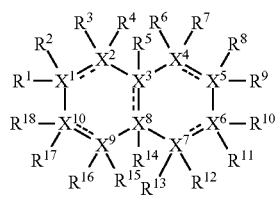

(I)

wherein:

$X^1$-$X^{10}$ are each independently either a C, N or O;

$R^1$-$R^{18}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence;

(b) Formula II

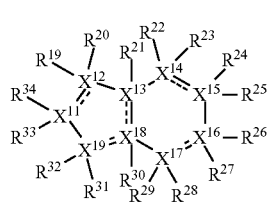

(II)

wherein:

$X^{11}$-$X^{19}$ are each independently either a C, N or O;

$R^{19}$-$R^{34}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence;

(c) Formula III

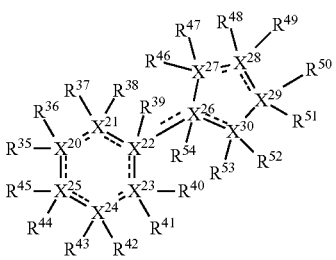

(III)

wherein, $X^{20}$-$X^{30}$ are each independently either a C, N or O;

$R^{35}$-$R^{54}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence;

(d) Formula IV

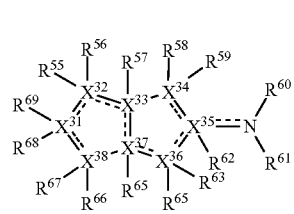
(IV)

wherein, $X^{31}$-$X^{38}$ are each independently either a C, N or O;

$R^{55}$-$R^{69}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence;

derivatives or analogs of Formulas I-IV thereof, including pharmaceutical salts and prodrugs; and wherein the compound has antimicrobial activity.

In another embodiment, the disclosure provides for compound comprising at least 5 carbon atoms, at least 5 nitrogen atoms, at least 5 hydrogen atoms, and at least one oxygen atom and is selected from the group comprising:

(a) Formula I:

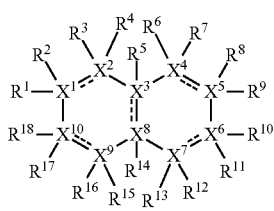
(I)

wherein:

$X^1$-$X^{10}$ are each independently either a C, N or O;

$R^1$-$R^{18}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence;

(b) Formula II

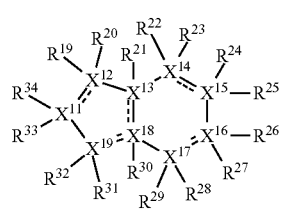
(II)

wherein:

$X^{11}$-$X^{19}$ are each independently either a C, N or O;

$R^{19}$-$R^{34}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence;

(c) Formula III

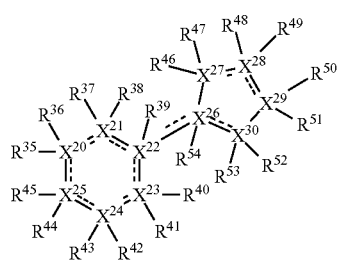
(III)

wherein, $X^{20}$-$X^{30}$ are each independently either a C, N or O;

$R^{35}$-$R^{54}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence;

(d) Formula IV

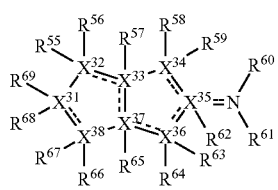
(IV)

wherein, $X^{31}$-$X^{38}$ are each independently either a C, N or O;

$R^{55}$-$R^{69}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-

$C_2$)alkynyl, hydroxyl, ketone, aldehyde, ester, ether, amide, amine, imine, imide, nitrate, nitrile, nitro, nitroso, and no atom if bound to X that has reached its maximum valence;

derivatives or analogs of Formulas I-IV thereof, including pharmaceutical salts and prodrugs; and wherein the compound has antimicrobial activity.

In a further embodiment, the disclosure provides for compound comprising at least 5 carbon atoms, at least 5 nitrogen atoms, at least 5 hydrogen atoms, and at least one oxygen atom and is selected from the group comprising:

(a) Formula I(a):

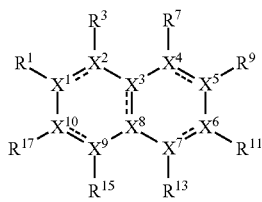

wherein:

$X^1$-$X^{10}$ are each independently either a C, N or O;

$R^1$, $R^3$, $R^7$, $R^9$, $R^{11}$, $R^{13}$, $R^{15}$, and $R^{17}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$)alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence;

(b) Formula II(a)

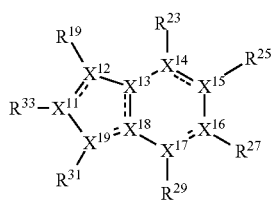

wherein:

$X^{11}$-$X^{19}$ are each independently either a C, N or O;

$R^{19}$, $R^{23}$, $R^{25}$, $R^{27}$, $R^{29}$, $R^{31}$, and $R^{33}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$)alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence;

(c) Formula III(a)

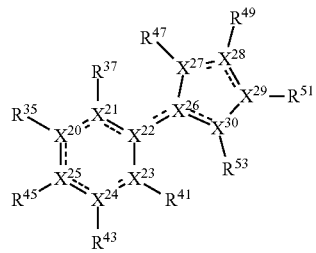

wherein, $X^{20}$-$X^{30}$ are each independently either a C, N or O;

$R^{35}$, $R^{37}$, $R^{41}$, $R^{43}$, $R^{45}$, $R^{47}$, $R^{49}$, $R^{51}$, and $R^{53}$, are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$) alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence;

(d) Formula IV(a)

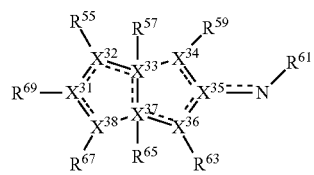

wherein, $X^{31}$-$X^{38}$ are each independently either a C, N or O;

$R^{55}$, $R^{57}$, $R^{59}$, $R^{61}$, $R^{63}$, $R^{65}$, $R^{67}$, and $R^{69}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$) alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence;

derivatives or analogs of Formulas I(a)-IV(a) thereof, including pharmaceutical salts and prodrugs; and wherein the compound has antimicrobial activity.

In yet a further embodiment, the disclosure provides for a compound selected from the group comprising:

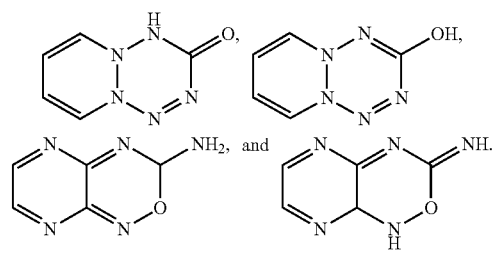

In a certain embodiment, the disclosure provides for a compound selected from the group comprising:

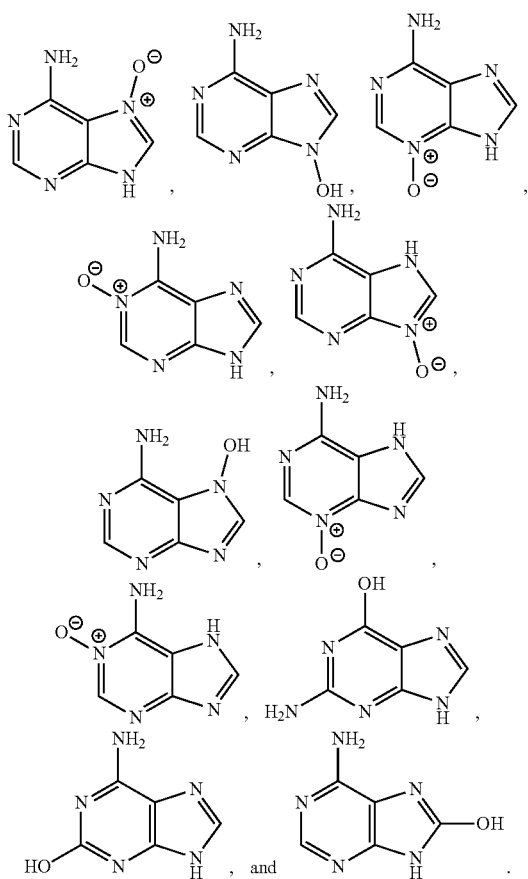

In another embodiment, the disclosure provides for a compound having a structural formula of:

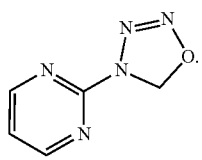 [SMILES: c1cnc(N2CON=N2)nc1]

In yet another embodiment, the disclosure provides for a compound having a structural formula of:

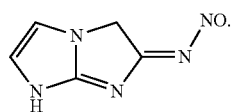

The disclosure also provides a method to use any one or more of the compounds above to treat MRSA, as well as group A *streptococcus* (GAS) and group B *streptococcus* (GBS) and *Staphylococcus aureus* (*S. aureus*) infections, which are the most common pathogens in human skin. Thus, a firmocidin of the disclosure can be used for antibiotic treatment to control skin infections.

In a particular embodiment, the disclosure provides for inhibiting the growth of a bacterium or fungus comprising contacting the bacterium or fungus with an inhibiting effective amount of a composition comprising a compound disclosed herein. In another embodiment, the disclosure provides for contacting the bacterium or fungus is either in vitro or in vivo, such as where the contacting in vivo is through topical administration. In a further embodiment, the disclosure provides for inhibiting the growth of a bacterium that is either gram positive or gram negative. In another embodiment, the disclosure provides for a composition comprising the compound disclosed herein with at least one additional antimicrobial agent. In yet another embodiment, the disclosure provides for a composition comprising the compound disclosed herein with a pharmaceutically acceptable carrier.

As described more fully herein, firmocidin suppresses growth of methicillin-resistant *S. aureus* (MRSA), a strain that is highly resistant to some antibiotics. Existing antibiotic therapies can non-specifically kill bacteria, which may disrupt the homeostasis of skin-resident microflora. However, Firmocidin does not affect the growth of *S. epidermidis* which contributes normal defense at the skin epithelium. Firmocidin also did not affect viability of human keratinocytes and sebocytes. In addition, Firmocidin is isolated from a microorganism residing in the normal skin microflora, suggesting low toxicity to the host. Thus, Firmocidin can be safely used as a pathogen-specific antibiotic therapy for skin infections.

In a particular embodiment, the disclosure provides a method for treating an infection, including infections caused by bacteria, fungus, parasites or viruses, or a dermatological disorder, including dermatological disorders such as, wounds, diabetic ulcers, acne, rosacea, atopic dermatitis, pyodermas, and burn wounds, by administering an effective amount of a firmocidin compound disclosed herein. The disclosure also provides for a composition formulated for systemic or topical administration.

In another embodiment, the Firmocidin of the disclosure comprises an NMR spectra as set forth in FIGS. 9 and 10. The firmocidin NMR did not match any previously characterized antimicrobial agents, suggesting firmocidin is a novel antimicrobial component. In vitro bactericidal assays revealed that firmocidin showed antimicrobial activity against Group A *streptococcus*, Group B *streptococcus* and *Staphylococcus aureus*, which are the most common pathogens in the human skin.

The disclosure provides for a firmocidin compound that has approximately the physical and structural properties as presented in FIGS. 1-10 and the biological properties as presented in FIGS. 12-14. There is provided, in some embodiments, a firmocidin compound, prepared from a cultured strain of *S. epidermidis* having a molecular ionic mass [M+H]$^+$ of about 152.0567 and wherein the antimicrobial agent inhibits the growth of Group A streptococcus (GAS), Group B streptococcus (GBS), *S. aureus*, while not inhibiting the growth of *S. epidermidis*. In some embodiments, the agent has at least one hydroxyl group. In some embodiments, the firmocidin compound's EI-MS spectrum has m/z fragment peaks of about at 54.2, 66.2, 81.2, 91.2, 93.1, 108.1, 121.1, 134.1, 135.1, 136.1, and 151.1. In some embodiments, the firmocidin compound is not cytotoxic to HaCaT cells or SZ95 sebocyte cells when used at concentrations of 100 ug/ml or less. In some embodiments, the firmocidin compound has the molecular formula of $C_5H_5N_5O$.

In a certain embodiment, a pharmaceutical composition comprising a firmocidin compound disclosed herein further comprises one or more pharmaceutically acceptable carriers.

In another embodiment, the disclosure provides for a pharmaceutical composition comprising a compound disclosed herein which is formulated for oral, parenteral, or topical administration. In another embodiment, the disclosure provides for a pharmaceutical composition comprising a compound disclosed herein for topical administration wherein the topical dosage form is either in the form of a cream, ointment, gel, spray or lotion.

In a certain embodiment, the disclosure provides for a composition comprising a compound disclosed herein and further comprises one or more additional therapeutic agents, including antibiotics, sepsis treatments, steroidal drugs, antifungal agents, and antipruritics. Examples of antibiotics, include, but are not limited to, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, clofazimine, cloxacillin, colistin, dalfopristan, demeclocycline, dicloxacillin, dirithromycin, doxycycline, erythromycin, enafloxacin, enviomycin, ertepenem, ethambutol, flucloxacillin, fosfomycin, furazolidone, gatifloxacin, geldanamycin, gentamicin, herbimicin, imipenem, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, oxytetracycline, penicillin, piperacillin, platensimycin, polymixin B, prochlorperazine, prontocil, quinupristine, rifabutin, roxithromycin, spectinomycin, sulfacetamide, sulfamethizole, sulfamethoxazole, teicoplanin, telithromycin, tetracycline, thioacetazone, thioridazine, ticarcillin, tobramycin, trimethoprim, troleandomycin, trovafloxacin, and vancomycin.

In yet another embodiment, the disclosure provides a method for the treatment, prevention, or amelioration of one or more symptoms of an infection by a foreign agent or a dermatological disorder comprising administering a therapeutically effective amount of a firmocidin compound disclosed herein. Examples of foreign agents, include, but are not limited to, bacterium, parasite, virus, or fungus. Bacteria that can be affected by the use of a compound, derivative or analog thereof, including pharmaceutical salt and prodrug forms, include both gram-negative and gram-positive bacteria. For example, bacteria that can be affected include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthraces, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia*, and *Campylobacter jejuni*. In a preferred embodiment, the bacterium is selected from the group comprising Group A *streptococcus* (GAS), Group B *streptococcus* (GBS), and *S. aureus*.

In another embodiment, the disclosure provides a method of treatment for an infection caused by a fungus by administering a compound described herein, derivative or analog thereof, including pharmaceutical salt and prodrug forms. Examples of fungal organisms may be affected, include for example, *Microsporum canis* and other *Microsporum* sp.; *Trichophyton* sp. such as *T. rubrum*, and *T. mentagrophytes*, yeasts, e.g., *Candida albicans, C. Tropicalis*, or other *Candida* species, *Saccharomyces cerevisiae, Torulopsis glabrata, Epidermophyton floccosum, Malassezia furfur (Pityropsporon orbiculare*, or *P. ovale, Cryptococcus neoformans, Aspergillus fumigatus, Aspergillus nidulans*, and other *Aspergillus* sp., Zygomycetes, e.g., *Rhizopus, Mucor, Paracoccidioides brasiliensis, Blastomyces dermatitides, Histoplasma capsulatum, Coccidioides immitis*, and *Sporothrix schenckii*.

BRIEF DESCRIPTION OF THE DRAWINGS

FIG. 11 provides that compounds labeled 1-7, which have the molecular formula of C$_5$H$_5$N$_5$O, but were not antimicrobial agents for GAS. Each compound was dissolved or suspended in PBS at 2 mg/mL and 5 mL was applied on an agar plate inoculated with GAS (NZ131).

DETAILED DESCRIPTION

Figure 1:
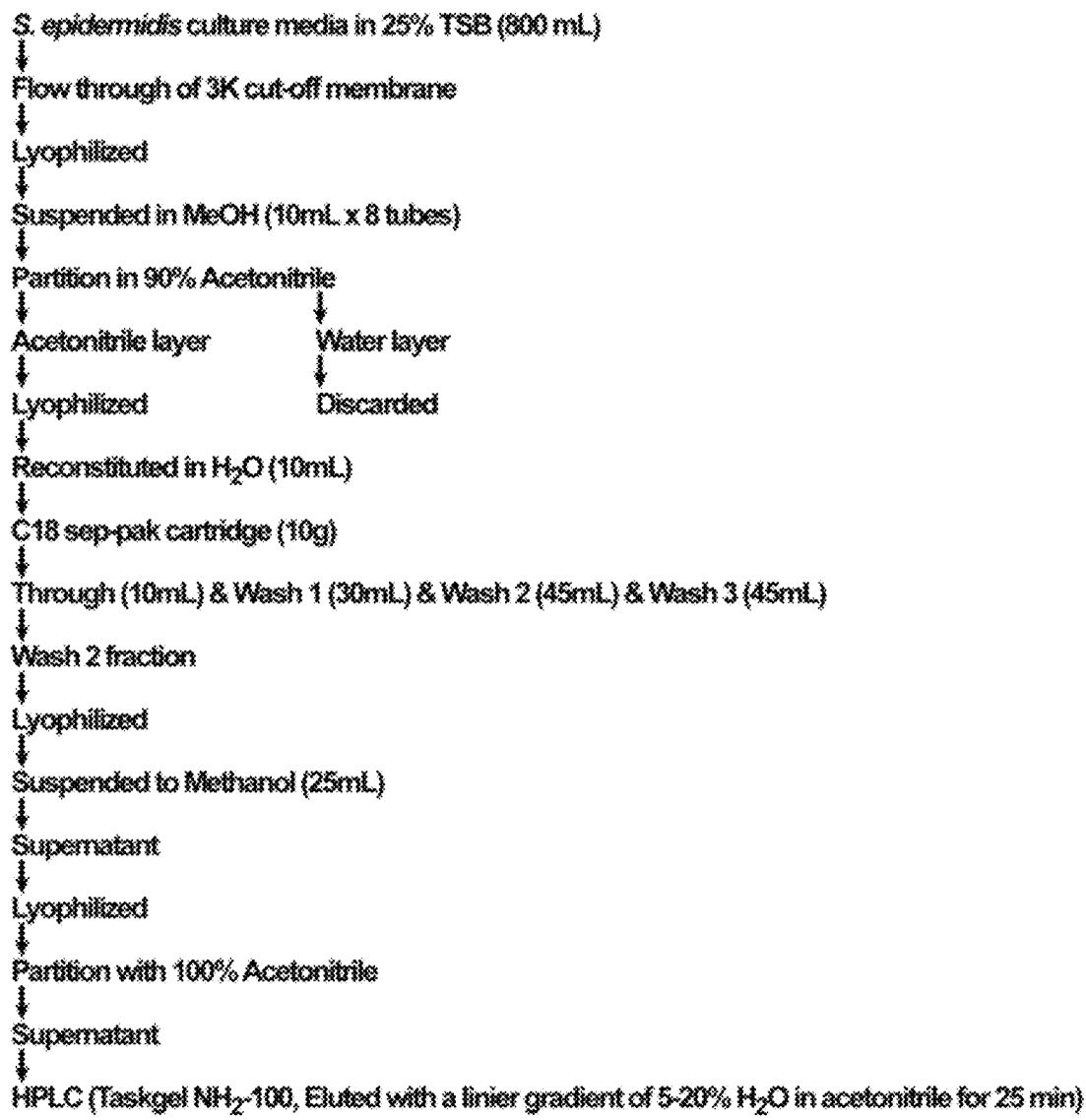
FIG. 1 presents a flow chart for the preparation of firmocidin from a culture supernatant of *S. epidermidis*.

As used herein and in the appended claims, the singular forms "a," "and," and "the" include plural referents unless the context clearly dictates otherwise. Thus, for example, reference to "a compound" includes a plurality of such compounds and reference to "the cell" includes reference to one or more cells and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

The term "alkyl", refers to an organic group that is comprised of carbon and hydrogen atoms that contains single covalent bonds between the carbons. Generally, an "alkyl" as used in this disclosure, refers to an organic group that contains 1 to 20 carbon atoms, unless stated otherwise. Wherein if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Specific substituted alkyl groups include haloalkyl groups, particularly trihalomethyl groups and specifically trifluoromethyl groups.

The term "alkenyl", refers to an organic group that is comprised of carbon and hydrogen atoms that contains at least one double covalent bond between two carbons. Generally, an "alkenyl" as used in this disclosure, refers to organic group that contains 1 to 20 carbon atoms, unless stated otherwise. While a $C_1$-alkenyl can form a double bond to an atom of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise. Substituted alkenyl groups include among others those which are substituted with alkyl or aryl groups, which groups in turn can be optionally substituted. Specific alkenyl groups include ethenyl, prop-1-enyl, prop-2-enyl, but-1-enyl, but-2-enyl, pent-1-enyl, pent-2-enyl, branched pentenyl, hex-1-enyl, branched hexenyl, all of which are optionally substituted.

The term "alkynyl", refers to an organic group that is comprised of carbon and hydrogen atoms that contains a triple covalent bond between two carbons. Generally, an "alkynyl" as used in this disclosure, refers to organic group that contains 1 to 20 carbon atoms, unless stated otherwise. While a $C_1$-alkynyl can form a triple bond to an atom of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A "cycloalkyl" can also include bicyclic and tricyclic-based groups. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof "Cycloalkenyl" can include bicyclic and tricyclic-based groups. A cycloalkenyl may be substituted or unsubstituted, or in the case of more than one cycloalkenyl ring, one or more rings may be unsubstituted, one or more rings may be substituted, or a combination thereof. Specific alkenyl groups include cycloprop-1-enyl, cyclobut-1-enyl, cyclobut-2-enyl, cyclopent-1-enyl, cyclohexenyl, all of which are optionally substituted.

The term "aryl", as used in this disclosure, refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. Substituted aryl groups include among others those which are substituted with alkyl or alkenyl groups, which groups in turn can be optionally substituted. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups. Specific aryl groups include phenyl groups, biphenyl groups, and naphthyl groups, all of which are optionally substituted.

The term "heterocycle", as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be heteroaryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1] heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing a hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2, 3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but are not limited to, quinuclidinyl, diazabicyclo[2.2.1]heptyl; and 7-oxabicyclo[2.2.1]heptyl.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and 0.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents. For example, optionally substituted hydrocarbons, hetero-hydrocarbons, heterocycles, mixed ring systems, and the like, can include substitution with one or more of the following substituents: halogens, CN, —COOR, —OR, —COR, —OCOOR, —CON(R)$_2$, —OCON(R)$_2$, —N(R)$_2$, NO$_2$, —SR, —SO$_2$R, —SO$_2$N(R)$_2$ or —SOR groups, wherein R is selected from the group comprising a hydrocarbon, a hetero-hydrocarbon, heterocycle, and mixed ring system. Optional substitution of alkyl groups includes substitution with one or more alkenyl groups, aryl groups or both, wherein the alkenyl groups or aryl groups are also optionally substituted. Optional substitution of alkenyl groups includes substitution with one or more alkyl groups, aryl groups, or both, wherein the alkyl groups or aryl groups are also optionally substituted. Optional substitution of aryl groups includes substitution of the aryl ring with one or more alkyl groups, alkenyl groups, or both, wherein the alkyl groups or alkenyl groups are also optionally substituted.

The term "substituent" refers to an atom or group of atoms substituted in place of a hydrogen atom. For purposes of this disclosure, a substituent would include deuterium atoms.

Optional substituents for hydrocarbons, hetero-hydrocarbons, heterocycles, mixed ring systems, and the like, include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds;
—SR, —SO$_2$R, or —SOR where R is an alkyl group or an aryl groups and more specifically where R is methyl, ethyl, propyl, butyl, phenyl groups all of which are optionally substituted; for example —SR, R can be hydrogen;
—OCOOR where R is an alkyl group or an aryl groups;
—SO$_2$N(R)$_2$ where R is a hydrogen, an alkyl group, or an aryl group and R and R can form a ring; and
—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates that the bond may be a single covalent bond or alternatively a double covalent bond. But in the case where a ring atom's maximum valence would be exceeded by forming a double covalent bond with another ring atom, then the bond would be a single covalent bond.

For the purposes of this disclosure, in the instance that a ring atom designated as X would exceed its maximum valence by binding a group designated by R, then the group designated by R would be absent.

The term "antimicrobial" as it relates to treatments, agents, and compounds refers to an agent that can be used to suppress, attenuate, ameliorate, any symptom caused by or resulting from an infection by a foreign agent. For the purposes of this disclosure a foreign agent includes, but is not limited to, bacteria, parasites, viruses, and fungi.

Infections from organisms such as Group A *Streptococcus* (GAS, *Streptococcus pyogenes*) or *Staphylococcus aureus* range from superficial to invasive, and collectively represent a severe societal burden, only escalating with the increase of resistance to pharmaceutically derived antibiotics (Jones, 2003; Carapetis et al., 2005; McCaig et al., 2006). Increasing the understanding of innate host-derived antimicrobial peptides (AMPs) offers an alternative to the development of treatment of such infections, as AMPs have retained the capacity to provide protection against infections by GAS, *S.*

*aureus*, and other microbes (Dorschner et al., 2001; Nizet et al., 2001; Di Nardo et al., 2008), and have not lost their antimicrobial relevance as in the case of many pharmaceutical antibiotics.

A surprising recent revelation is that the AMPs that occupy the surface of the skin are made not only by the host cell, but also in prokaryotic organisms that inhabit the host's epidermis. A large number of Gram positive bacteria such as *Lactococcus, Streptococcus* and *Streptomyces* species have been known to produce factors to inhibit other bacteria (Bastos et al., 2009). Proteinaceous factors produced by bacteria with bactericidal activity against the growth of similar or closely related bacterial strains are called bacteriocins. *S. epidermidis*, the dominant commensal bacterium found in the skin microflora, produces various types of bacteriocins. Most of these peptides are encoded in plasmids. Epidermin, Pep5 and epilancin K7 are the most characterized bacteriocins isolated from *S. epidermidis* (Bastos et al., 2009). Because of their potential to kill pathogens in vitro, these bacteriocins may possess the capacity to provide antimicrobial protection against pathogens on the skin surface. Research has shown unique peptides phenol-soluble modulin (PSM)γ and PSMδ produced by *S. epidermidis* could be beneficial to the host and thus serve as additional AMPs on normal skin surface (Cogen et al., 2010). These peptides selectively exhibited bactericidal activity against skin pathogens, such as *Staphylococcus aureus* (*S. aureus*), Group A *Streptococcus* (GAS) and *Escherichia coli*, whereas they are not active against *S. epidermidis*. Moreover, inoculating PSMs on the mouse skin surface reduced GAS but not the survival of *S. epidermidis*. This selective activity is likely to be an important part of a normal microbial defense strategy against colonization.

*Staphylococcus epidermis* (*S. epidermidis*) is a major constituent of microflora on healthy human skin. Recent studies indicate that *S. epidermidis* protect human skin by preventing pathogenic infections by producing phenol-soluble modulins (PSMs), which function as antimicrobial peptides. In addition, lipoteichoic acid produced by *S. epidermidis* benefits human skin by suppressing skin inflammation during wound repair.

The disclosure provides a novel antimicrobial molecule from culture supernatant of a clinically isolated strain of *S. epidermidis* (MO34). The predicted molecular formula is $C_5H_5N_5O$. The compound is referred to herein as "firmocidin." Firmocidin exerts antimicrobial activities against group A streptococcus (GAS) and group B streptococcus (GBS) and *Staphylococcus aureus* (*S. aureus*), which are most common pathogens in human skin. Thus, firmocidin can be used as an antimicrobial treatment to control skin infections.

Figure 3:
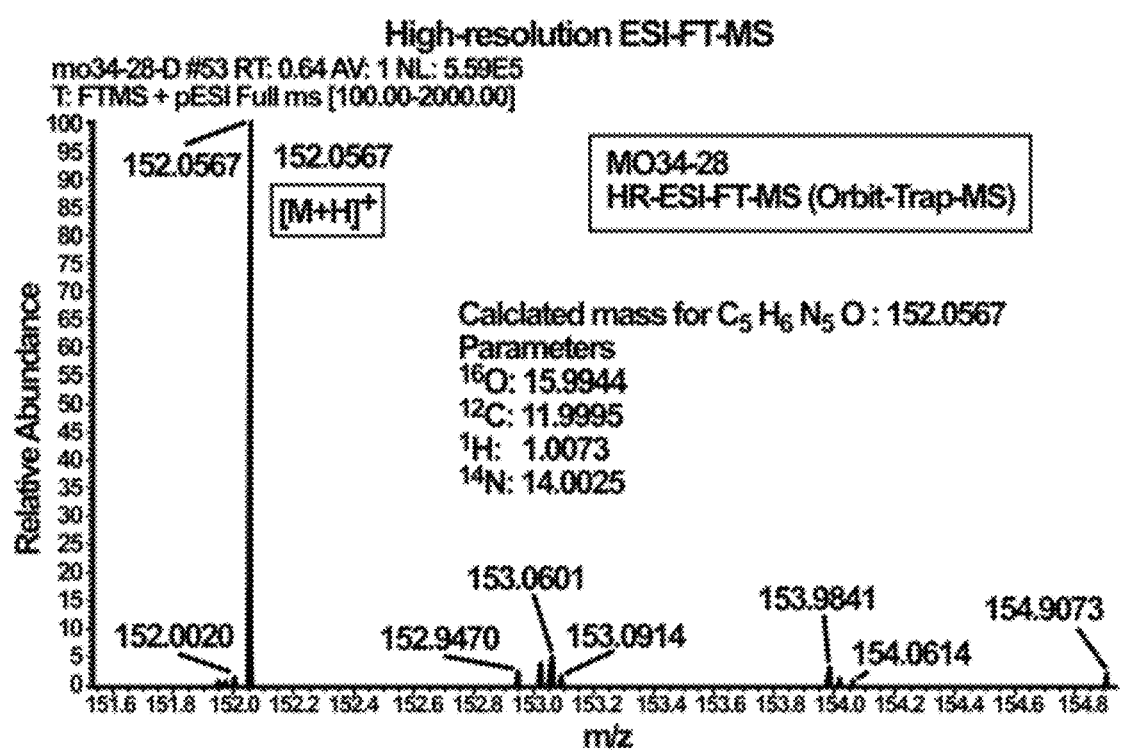
FIG. 3 presents a chromatogram of firmocidin using high-resolution ESI-FT-MS. The mass spectra indicate that firmocidin has a molecular mass of 152.0567. Based on the mass spectrum, firmocidin has a predicted structure of 5 carbon atoms, 5 hydrogen atoms, 5 nitrogen atoms, and 1 oxygen atom.
Figure 9:
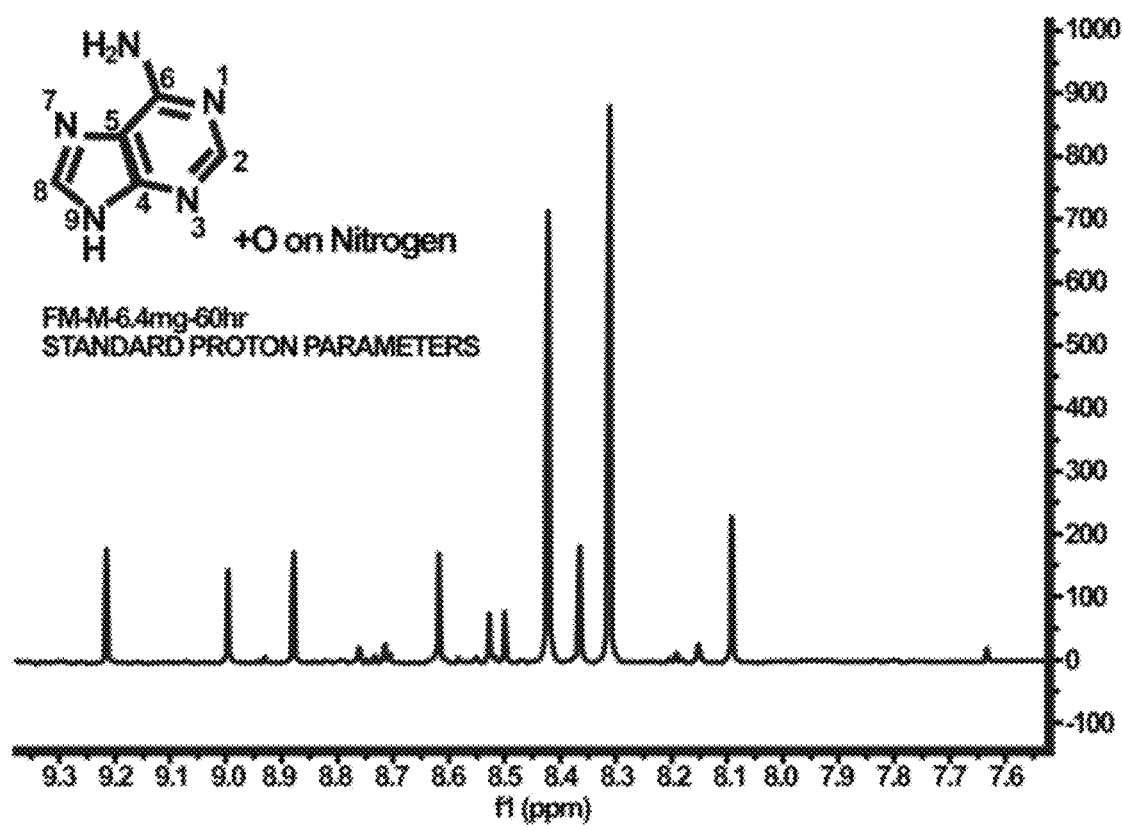
FIG. 9 presents a $^1$H NMR spectrum of firmocidin. The chemical shifts obtained are identical to an adenine-N-oxide.
Figure 10:
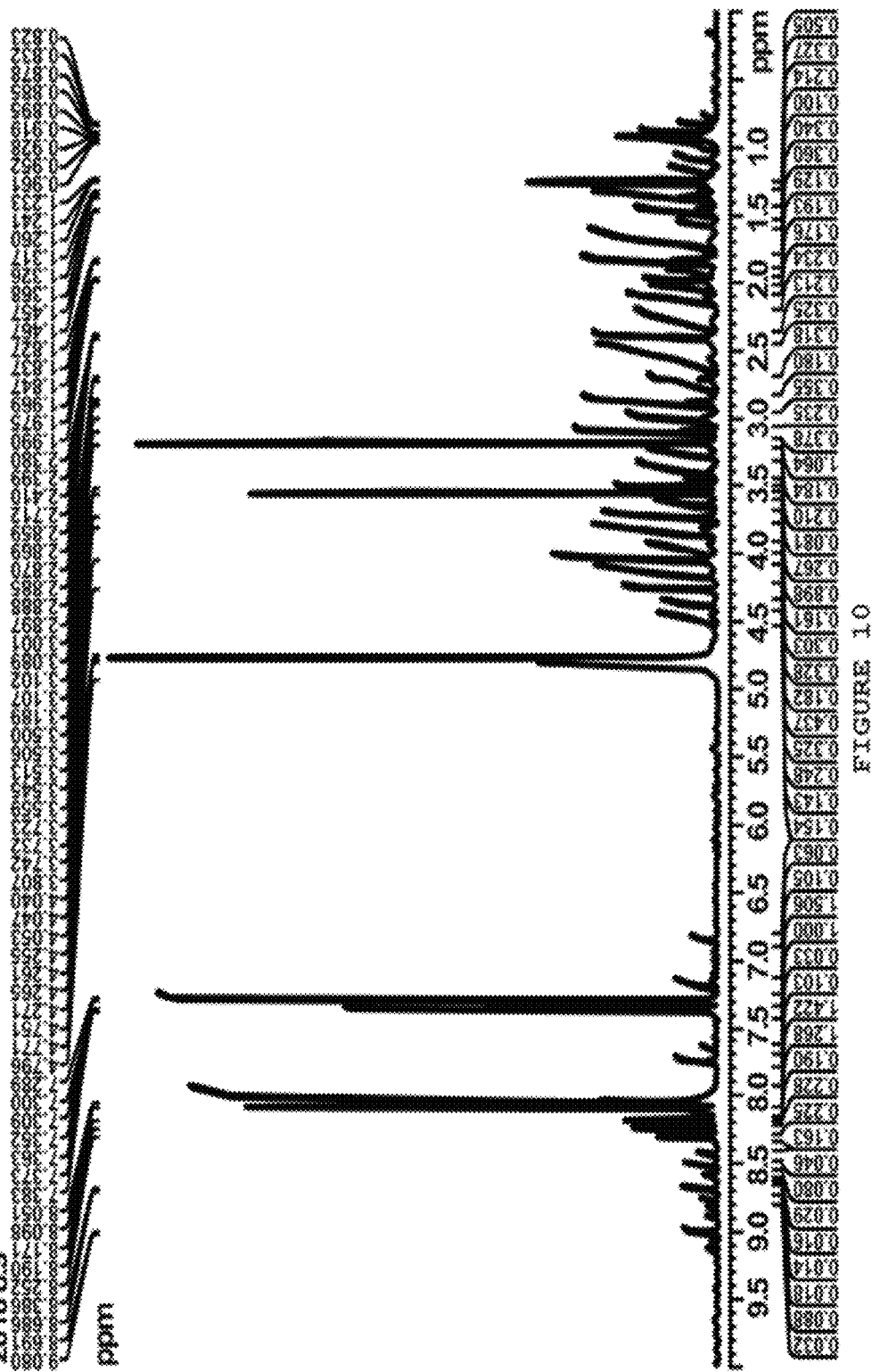
FIG. 10 presents a $^1$H NMR spectrum of firmocidin. The characteristic nuclear shifts of a benzene ring appear at 8.0-8.5 ppm.
Figure 12:
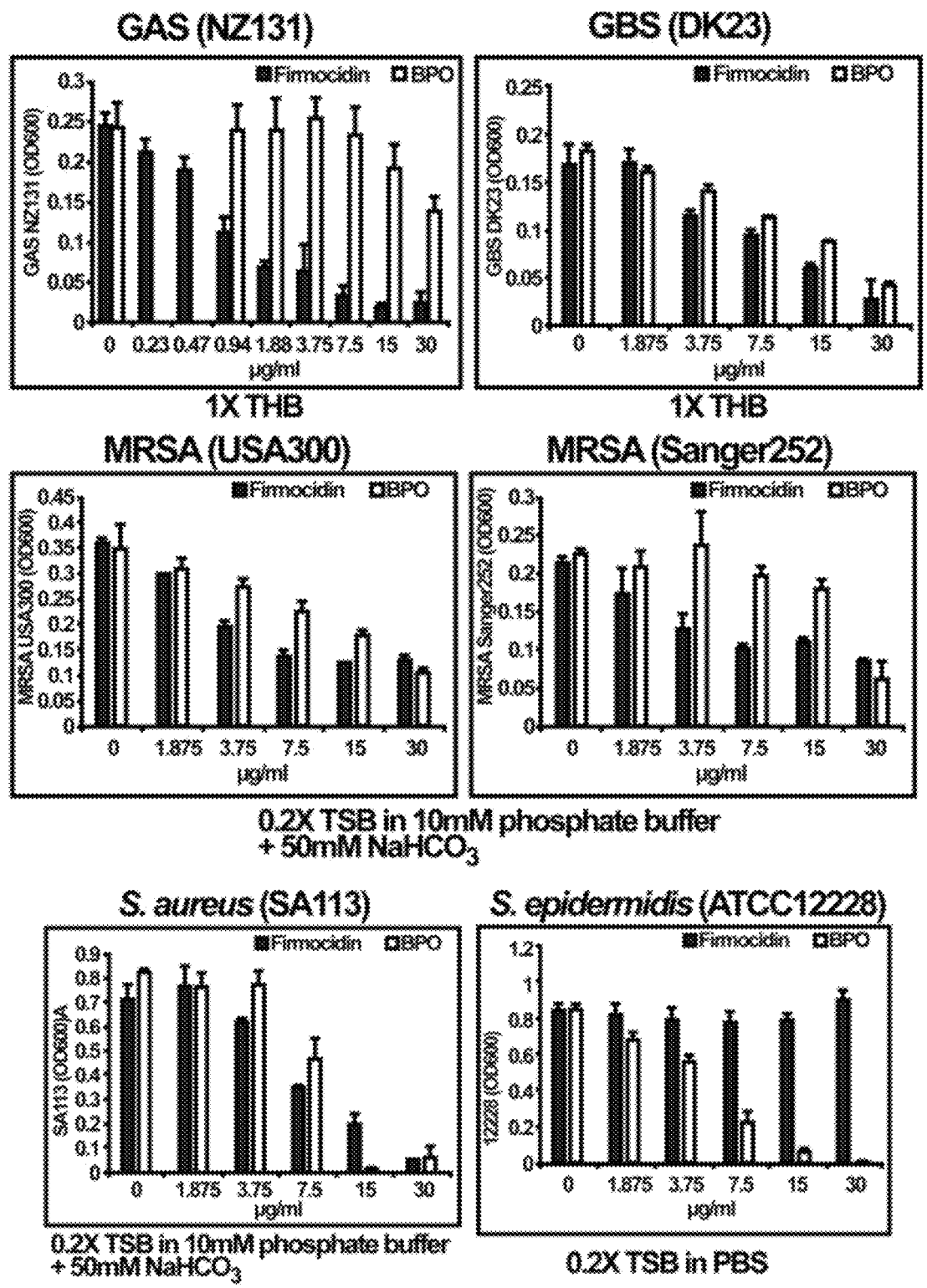
FIG. 12 presents data demonstrating firmocidin inhibits growth of various pathogens but not *S. epidermidis*. The data also show that firmocidin antimicrobial activity is superior to benzoyl peroxide (BPO). HPLC-purified firmocidin was incubated with various bacteria ($1 \times 10^6$ CFU/mL) in the indicated medium for 7 hrs. BPO was used as a positive control. After incubation, $OD_{600}$ was determined to estimate bacteria growth.

NMR spectra data of firmocidin did not match any previously characterized antimicrobial agents, suggesting firmocidin is a novel antimicrobial component (see, e.g., FIGS. 3, 9 and 10). In vitro bactericidal assays revealed that firmocidin showed antimicrobial activity against GAS, GBS and *Staphylococcus aureus*, which are most common pathogens in the human skin (see, e.g., FIG. 12). Most notably, firmocidin suppresses growth of methicillin-resistant *S. aureus* (MRSA), a strain that is highly resistant to some antibiotics (see, e.g., FIG. 12).

Existing antibiotic therapies are non-specific bactericidals that may disrupt the homeostasis of skin-resident microflora. However, firmocidin does not affect the growth of *S. epidermidis*, which contributes normal defense at the skin epithelium. Firmocidin also did not affect viability of human keratinocytes and sebocytes (see, e.g., FIG. 14). In addition, firmocidin is isolated from a microorganism residing in the normal skin microflora, suggesting low toxicity to the host. Thus, firmocidin can be safely used as a pathogen-specific antimicrobial therapy for skin infections.

Figure 2:
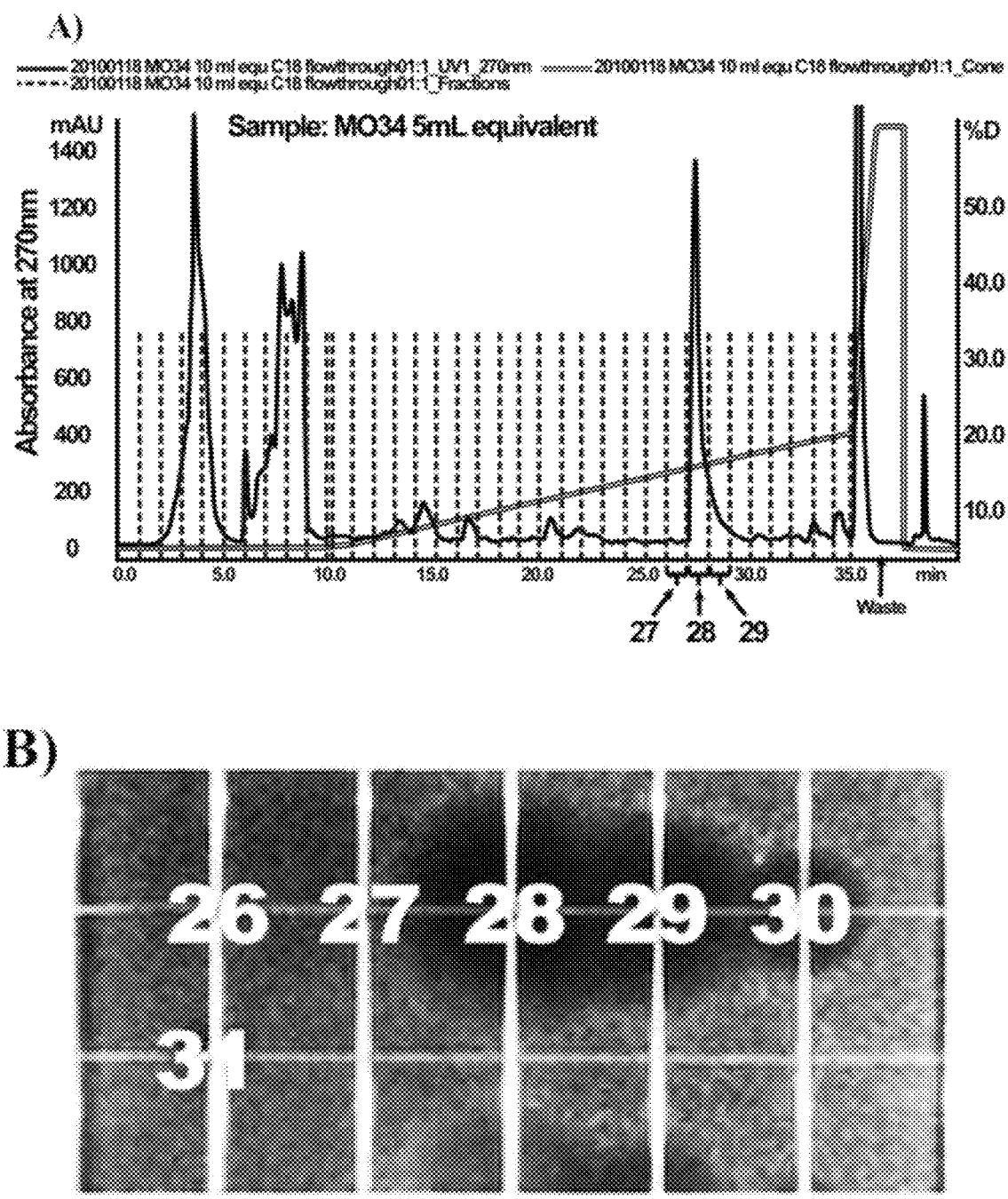
FIG. 2A-B presents the purification of firmocidin from the culture supernatant of *S. epidermidis* by HPLC and the activity of certain indicated fractions. The crude culture supernatant *S. epidermidis* was applied to a TaskGel NH$_2$-100 column (4.5 mm×150 mm) and eluted with a 25-min linear gradient of 5-20% H$_2$O in acetonitrile at a flow rate of 1 ml/min; the eluent was monitored at 270 nm (FIG. 2A). Fractions 26-31 were lyophilized, reconstituted in PBS and applied on an agar plate inoculated with GAS (NZ131) (FIG. 2B). Clear zones demonstrate antimicrobial activity.

The disclosure also provides a procedure for purification of firmocidin from culture supernatant of *S. epidermidis* (see e.g., FIG. 1). The sample was purified by HPLC using a Taskgel $NH_2$-100 column (Tosoh) with a linear gradient of 5-20% water in acetonitrile (see e.g., FIG. 2). A peak at the fraction #28 showed antimicrobial activity (see, e.g., FIG. 2). High-resolution ES-MS analysis gave the molecular formula $C_5H_5N_5O$ (calculated exact mass for $[M+H]^+$ =152.0567, observed mass=152.0567) (see, e.g., FIG. 3). Antimicrobial activity of the authentic compounds possessing the molecular formula of $C_5H_5N_5O$ were tested, but none of them showed antimicrobial activity against GAS (see e.g., FIG. 11).

Figure 13:
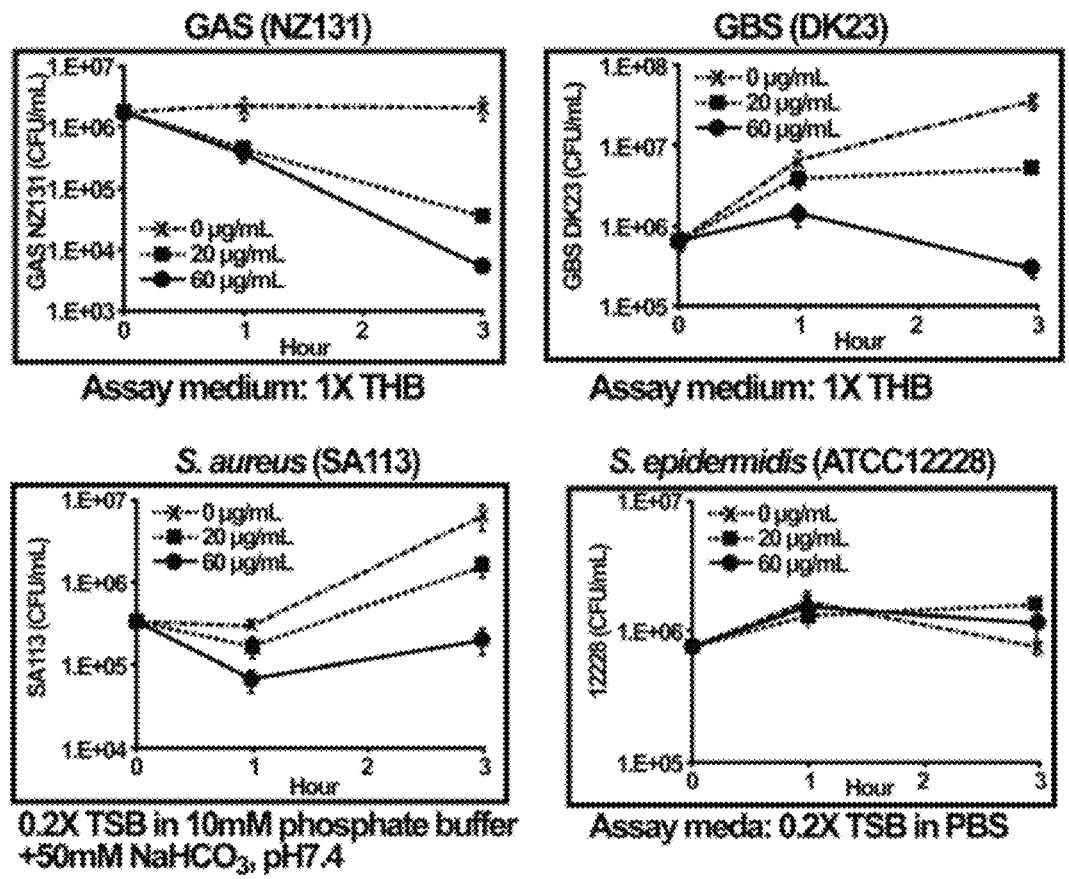
FIG. 13 presents data showing firmocidin's bactericidal activity against GAS and bacteristatic activity against GBS and *S. aureus*, but not *S. epidermidis*. Various bacteria ($1 \times 10^6$ CFU/mL) were incubated with HPLC-purified firmocidin (0, 20 and 60 mg/mL) in the indicated medium. Colony-forming unit (CFU) of the bacteria was determined at the indicated times by plating serial dilutions of bacteria suspension.

According to the preliminary data from NMR structural determination, the NMR spectra for firmocidin did not match to any of authentic antimicrobial agents. This suggests that firmocidin is a novel antimicrobial compound that suppresses the growth of GAS, GBS, methicillin-sensitive *S. aureus* and MRSA, but not *S. epidermidis* (see, e.g., FIG. 12) and Gram negative bacteria. Its antimicrobial activity was stronger than benzoyl peroxide (BPO), which is a frequently used topical medication. Furthermore, kinetic study of antimicrobial activity showed that firmocidin exhibits bactericidal activity against GAS and bacteristatic activity against GBS and *S. aureus* (see, e.g., FIG. 13), but not against *S. epidermidis*. However, firmocidin did not affect the viabilities of human keratinocytes and sebocytes (see, e.g., FIG. 14), suggesting low toxicity to the host. Thus, firmocidin is pathogen-specific and safe antimicrobial therapy for infections arising from GAS, GBS and *S. aureus*. Firmocidin, however, is likely to exert similar antimicrobial activity against other pathogens.

Methods and compositions useful for treatment of microbial infections are provided. In one embodiment the disclosure provides compositions and methods useful for treating a microbial infection wherein the methods and compositions comprise firmocidin, a derivative or salt thereof. For example, methods and compositions useful for the treatment of *S. aureus* infections, including those produced by methicillin- and vancomycin-resistant strains, are provided. The methods and compositions of the disclosure can be used alone or in combination with traditional antimicrobials and antibiotics to treat such infections. In addition, the methods and compositions disclosed herein can be used in settings such as foreign-body, catheter or endovascular infections, chronic osteomyeletis, hospital acquired or post-operative infections, recurrent skin infections, or for *S. aureus* infections in the immunocompromised host.

In a certain embodiment, the disclosure provides for a compound that is comprised of one or more ring structures that is comprised of at least 5 carbon atoms, at least 5 hydrogen atoms, at least 5 nitrogen atoms, and at least 1 oxygen atom, wherein the ring structures are optionally substituted and selected from the group comprising cycloalkyl, cycloalkenyl, cycloalkynyl, aryl, heterocycle, and mixed ring system. In another embodiment, the disclosure provides for a compound that is comprised of one or more ring structures that is comprised of 5 carbon atoms, 5 hydrogen atoms, 5 nitrogen atoms, and 1 oxygen atom, wherein the ring structures are optionally substituted and selected from the group comprising cycloalkyl, cycloalkenyl, cycloalkynyl, aryl, heterocycle, and mixed ring system. It should be understood for a heterocycle-, and a mixed ring system-based compound that while it may be preferable that one or more hetero-ring atoms is an N and/or O, the disclosure also provides for additional heteroatoms, including, but not limited to, N, O, S, Si, Al, B, and P. Likewise, it should also be understood for a compound comprised of a cycloalkyl, a cycloalkenyl, a cycloalkynyl, or an aryl, that while it may be preferable that these rings be substituted with either one or more oxygen containing functional groups, nitrogen containing functional groups, or a combination thereof, the disclosure also provides for a compound comprised of a cycloalkyl, a cycloalkenyl, a cycloalkynyl, or an aryl, being substituted with functional groups which do not contain oxygen and/or nitrogen atoms.

In a particular embodiment, the disclosure provides for a compound having structural Formula I

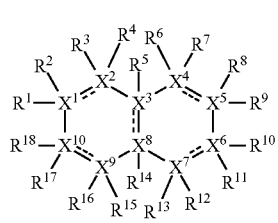

(I)

wherein, $X^1$-$X^{10}$ are each independently either a C, N or O;

$R^1$-$R^{18}$ are each independently selected from the group comprising H, D, optionally substituted ($C_1$-$C_6$)alkyl, optionally substituted ($C_1$-$C_6$)alkenyl, optionally substituted ($C_1$-$C_6$)alkynyl, optionally substituted hetero-($C_1$-$C_6$)alkyl, hetero-($C_1$-$C_6$)alkenyl, optionally substituted hetero-($C_1$-$C_6$)alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence.

In an additional embodiment, the disclosure provides for a compound having structural Formula I:

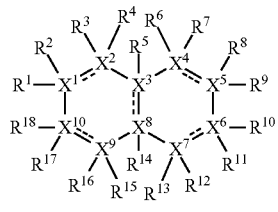

(I)

wherein, $X^1$-$X^{10}$ are each independently either a C, N or O;

$R^1$-$R^{18}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$)alkenyl, optionally substituted hetero-($C_1$-$C_2$)alkynyl, hydroxyl, ketone, aldehyde, ester, ether, amide, amine, imine, imide, nitrate, nitrile, nitro, nitroso, and no atom if bound to X that has reached its maximum valence; and wherein the compound has at least 5 carbon atoms, at least 5 hydrogen atoms, at least 5 nitrogen atoms, and at least 1 oxygen atom.

In a further embodiment, the disclosure provides for a compound having structural Formula I(a)

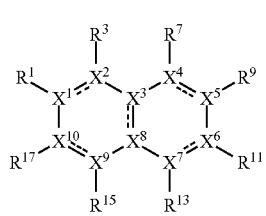

I(a)

wherein, $X^1$-$X^{10}$ are each independently either a C, N or O;

$R^1$, $R^3$, $R^7$, $R^9$, $R^{11}$, $R^{13}$, $R^{15}$, and $R^{17}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$)alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence; and wherein the compound has at least 5 carbon atoms, at least 5 hydrogen atoms, at least 5 nitrogen atoms, and at least 1 oxygen atom.

In a further embodiment, the disclosure provides for a compound having structural Formula I(a):

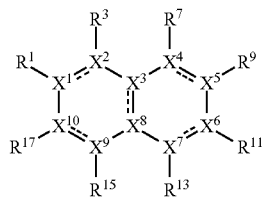

I(a)

wherein, $X^1$-$X^{10}$ are each independently either a C, N or O;

$R^1$, $R^3$, $R^7$, $R^9$, $R^{11}$, $R^{13}$, $R^{15}$, and $R^{17}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$)alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence; and wherein the compound has 5 carbon atoms, 5 hydrogen atoms, 5 nitrogen atoms, and 1 oxygen atom.

In yet a further embodiment, the disclosure provides for a compound selected from the group comprising

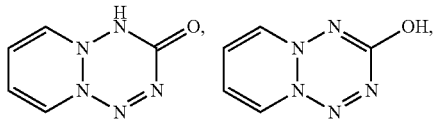

-continued

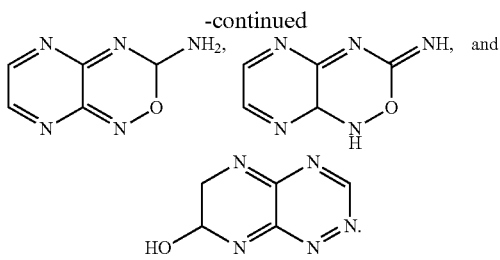

In a particular embodiment, the disclosure provides a compound having structural Formula II

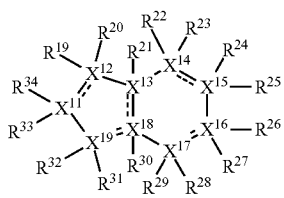
(II)

wherein,
$X^{11}$-$X^{19}$ are each independently either a C, N or O;
$R^{19}$-$R^{34}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence.

In another embodiment, the disclosure provides a compound having structural Formula II

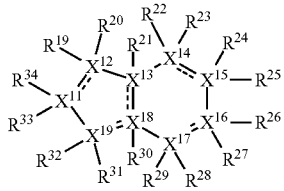
(II)

wherein,
$X^{11}$-$X^{19}$ are each independently either a C, N or O;
$R^{19}$-$R^{34}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence; and
wherein the compound has at least 5 carbon atoms, at least 5 hydrogen atoms, at least 5 nitrogen atoms, and at least 1 oxygen atom.

In yet another embodiment, the disclosure provides for a compound having structural Formula II(a):

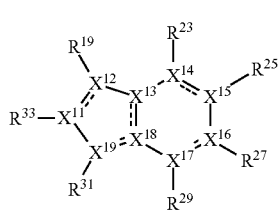
II(a)

wherein,
$X^{11}$-$X^{19}$ are each independently either a C, N or O;
$R^{19}$, $R^{23}$, $R^{25}$, $R^{27}$, $R^{29}$, $R^{31}$, and $R^{33}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, carbonate, amine, imine, nitrile, nitroso, and no atom if bound to X that has reached its maximum valence; and
wherein the compound has at least 5 carbon atoms, at least 5 hydrogen atoms, at least 5 nitrogen atoms, and at least 1 oxygen atom.

In a further embodiment, the disclosure provides for a compound having structural Formula II(a):

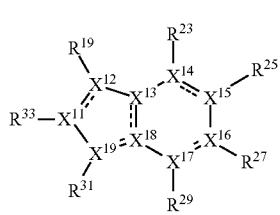
II(a)

wherein,
$X^{11}$-$X^{19}$ are each independently either a C, N or O;
$R^{19}$, $R^{23}$, $R^{25}$, $R^{27}$, $R^{29}$, $R^{31}$, and $R^{33}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, carbonate, amine, imine, nitrile, nitroso, and no atom if bound to X that has reached its maximum valence; and
wherein the compound has 5 carbon atoms, 5 hydrogen atoms, 5 nitrogen atoms, and 1 oxygen atom.

In a certain embodiment, the disclosure provides for a compound of selected from the group comprising

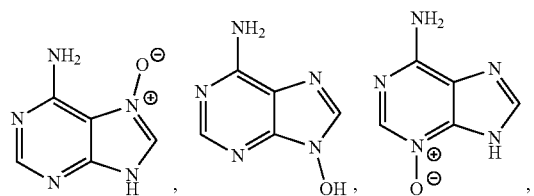

-continued

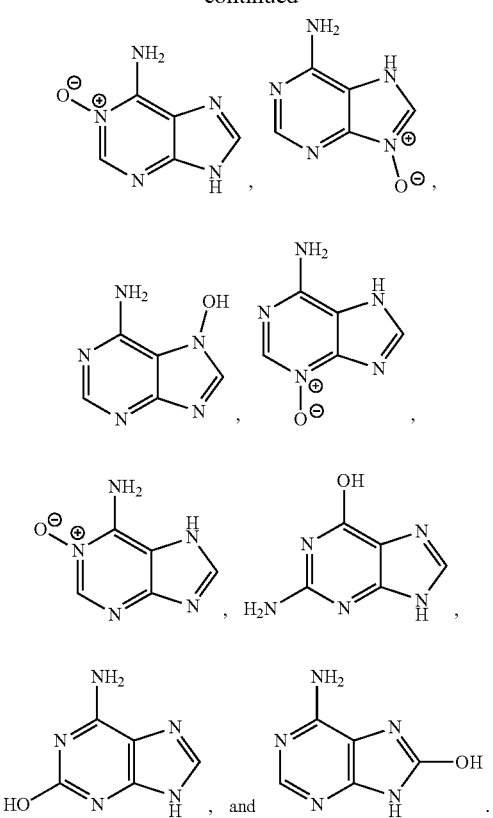

In a particular embodiment, the disclosure provides for a compound having structural Formula III:

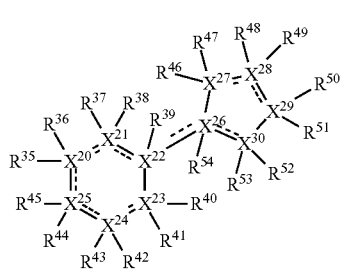

(III)

wherein, $X^{20}$-$X^{30}$ are each independently either a C, N or O;

$R^{35}$-$R^{54}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence; and wherein the compound has at least 5 carbon atoms, at least 5 hydrogen atoms, at least 5 nitrogen atoms, and at least 1 oxygen atom.

In a particular embodiment, the disclosure provides for a compound having structural Formula III:

In a further embodiment, the disclosure provides for a compound having structural Formula III(a)

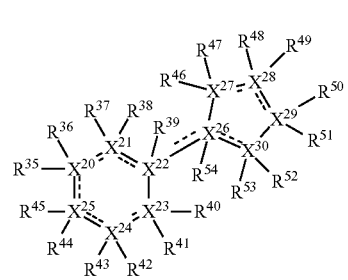

(III)

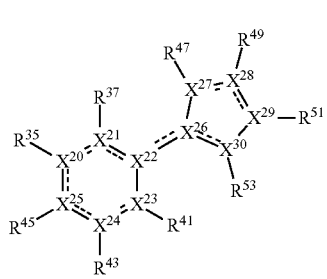

III(a)

wherein, $X^{20}$-$X^{30}$ are each independently either a C, N or O;

$R^{35}$-$R^{54}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence.

wherein, $X^{20}$-$X^{30}$ are each independently either a C, N or O;

$R^{35}$, $R^{37}$, $R^{41}$, $R^{43}$, $R^{45}$, $R^{47}$, $R^{49}$, $R^{51}$, and $R^{53}$, are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$ alkenyl, optionally substituted hetero-$(C_1$-$C_2)$alkynyl, hydroxyl, ketone, aldehyde, carbonate, amine, imine, nitrile, nitroso, and no atom if bound to X that has reached its maximum valence; and wherein the compound has at least 5 carbon atoms, at least 5 hydrogen atoms, at least 5 nitrogen atoms, and at least 1 oxygen atom.

In yet a further embodiment, the disclosure provides for a compound having structural Formula III(a):

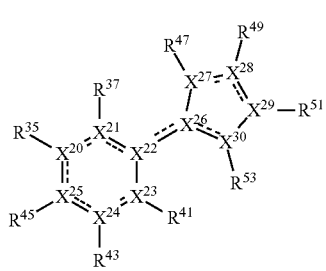

wherein, $X^{20}$-$X^{30}$ are each independently either a C, N or O;

$R^{35}$, $R^{37}$, $R^{41}$, $R^{43}$, $R^{45}$, $R^{47}$, $R^{49}$, $R^{51}$, and $R^{53}$, are each selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, carbonate, amine, imine, nitrile, nitroso, and no atom if bound to X that has reached its maximum valence; and wherein the compound has 5 carbon atoms, 5 hydrogen atoms, 5 nitrogen atoms, and 1 oxygen atom.

In yet a further embodiment, the disclosure provides for a compound having the structure of

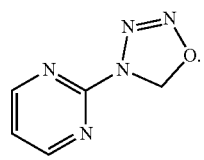 [SMILES: c1cnc(N2CON=N2)nc1]

In a particular embodiment, the disclosure provides for a compound having structural Formula IV:

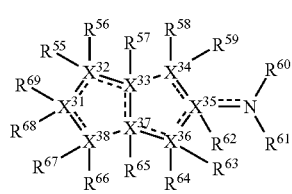

wherein, $X^{31}$-$X^{38}$ are each independently either a C, N or O;

$R^{55}$-$R^{69}$ are each independently selected from the group comprising H, D, optionally substituted $(C_1$-$C_6)$alkyl, optionally substituted $(C_1$-$C_6)$alkenyl, optionally substituted $(C_1$-$C_6)$alkynyl, optionally substituted hetero-$(C_1$-$C_6)$alkyl, hetero-$(C_1$-$C_6)$alkenyl, optionally substituted hetero-$(C_1$-$C_6)$alkynyl, halogen, hydroxyl, ketone, aldehyde, acyl halide, carbonate, carboxylic acid, ester, hydroperoxide, peroxide, ether, hemiacetal, hemiketal, acetal, orthoester, orthocarbonate ester, amide, amine, imine, imide, azide, diimide, cyanate, nitrate, nitrile, nitro, nitroso, thiol, sulfide, disulfide, sulfoxide, sulfone, sulfinic acid, sulfonic acid, thicyanate, thione, thial, phosphine, phosphonic acid, phosphate, phosphodiester, boronic acid, boronic ester, and no atom if bound to X that has reached its maximum valence.

In another embodiment, the disclosure provides a compound having structural Formula IV:

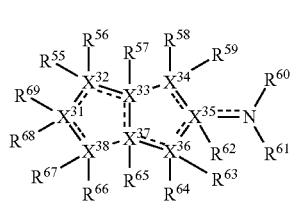

wherein, $X^{31}$-$X^{38}$ are each independently either a C, N or O;

$R^{55}$-$R^{69}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, ester, ether, amide, amine, imine, imide, nitrate, nitrile, nitro, nitroso, and no atom if bound to X that has reached its maximum valence; and wherein the compound has at least 5 carbon atoms, at least 5 hydrogen atoms, at least 5 nitrogen atoms, and at least 1 oxygen atom.

In yet another embodiment, the disclosure provides for a compound having structural Formula IV(a):

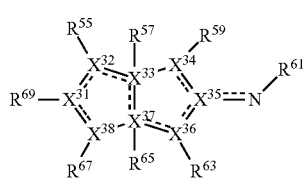

wherein, $X^{31}$-$X^{38}$ are each independently either a C, N or O;

$R^{55}$, $R^{57}$, $R^{59}$, $R^{61}$, $R^{63}$, $R^{65}$, $R^{67}$, and $R^{69}$ are each independently selected from the group comprising H, D, optionally substituted $(C_1$-$C_2)$alkyl, optionally substituted $(C_1$-$C_2)$alkenyl, optionally substituted $(C_1$-$C_2)$alkynyl, optionally substituted hetero-$(C_1$-$C_2)$alkyl, hetero-$(C_1$-$C_2)$alkenyl, optionally substituted hetero-$(C_1$-$C_2)$alkynyl, hydroxyl, ketone, aldehyde, carbonate, amine, imine, nitrile, nitroso, and no atom if bound to X that has reached its maximum valence; and wherein the compound has at least 5 carbon atoms, at least 5 hydrogen atoms, at least 5 nitrogen atoms, and at least 1 oxygen atom.

In a further embodiment, the disclosure provides for a compound having structural Formula IV(a):

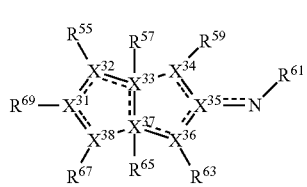

wherein, $X^{31}$-$X^{38}$ are each independently either a C, N or O;

$R^{55}$, $R^{57}$, $R^{59}$, $R^{61}$, $R^{63}$, $R^{65}$, $R^{67}$, and $R^{69}$ are each independently selected from the group comprising H, D, optionally substituted ($C_1$-$C_2$)alkyl, optionally substituted ($C_1$-$C_2$)alkenyl, optionally substituted ($C_1$-$C_2$)alkynyl, optionally substituted hetero-($C_1$-$C_2$)alkyl, hetero-($C_1$-$C_2$) alkenyl, optionally substituted hetero-($C_1$-$C_2$)alkynyl, hydroxyl, ketone, aldehyde, carbonate, amine, imine, nitrile, nitroso, and no atom if bound to X that has reached its maximum valence; and wherein the compound has 5 carbon atoms, 5 hydrogen atoms, 5 nitrogen atoms, and 1 oxygen atom.

In yet a further embodiment, the disclosure provides for a compound having the structure of

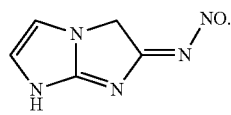

In yet a further embodiment, a compound disclosed herein that contains an acidic or basic moiety may also be disclosed as a pharmaceutically acceptable salt (See, Berge et al., *J. Pharma. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts, include, but are not limited to, aceptic acid, 2,2-dichoroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphtoic acid, nicotinic acid, nitric acid, oleic acid, orotic acid, oxalic acid, palmitic acid, pamoic acid, perchloric acid, phosphoric acid, L-pyroglutamic acid, saccharic acid, salicyclic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable acids for use in the preparation of pharmaceutically acceptable salts, include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-Lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Pharmaceutically acceptable salts comprise pharmaceutically-acceptable anions and/or cations. Pharmaceutically-acceptable cations include among others, alkali metal cations (e.g., Li+, Na+, K+), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl—, Br—), sulfate, acetates (e.g., acetate, trifluoroacetate), ascorbates, aspartates, benzoates, citrates, and lactate.

A compound disclosed herein may also have a prodrug form. A prodrug is a functional derivative of the compound disclosed herein and is readily convertible into the parent compound in vivo. Prodrugs are often useful because, in some situations, they may be easier to administer than the parent compound. They may, for instance, be bio-available by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). In a specific example, if a parent compound disclosed herein has a hydroxyl group, this hydroxyl group may be converted to an ester in attempts to increase bioavailability, solubility, injection site pain relief, elimination of an unpleasant taste, decreased toxicity, decreased metabolic inactivation, increased chemical stability, and/or prolonged or shortened action of the hydroxyl containing parent compound. In another specific example, if a parent compound disclosed herein has an amine group, this amine group may be converted to a Schiff base in attempts to increase bioavailability, solubility, injection site pain relief, elimination of an unpleasant taste, decreased toxicity, decreased metabolic inactivation, increased chemical stability, and/or prolonged or shortened action of the hydroxyl containing parent compound.

A pharmaceutical composition comprising a compound disclosed herein, a derivative or analog thereof, including pharmaceutical salt forms and prodrug forms, can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. A "therapeutically effective dose" is the quantity of an agent according to the disclosure necessary to prevent, to cure, or at least partially arrest the symptoms of an infection by a foreign agent. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of infections. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The disclosure provides for a compound disclosed herein, derivative or analog thereof, including pharmaceutical salt forms and prodrug forms, can be administered to any host, including a human or non-human animal, in an amount effective to inhibit the growth, spread or infection by a foreign agent. In one embodiment, the administration results in the inhibition of growth of a bacterium, virus, parasite and/or fungus. Thus, the methods and compositions are useful as antimicrobial agents.

Any of a variety of art-known methods can be used to administer a compound disclosed herein, a derivative or analog thereof, including pharmaceutical salt forms and prodrug forms, either alone or used in combination with one or more other therapeutic agents. For example, administration can be parenterally by injection or by gradual infusion over time. The agent(s) can be administered intravenously, intraperitoneally, intramuscularly, subcutaneously, intracavity, by inhalation, or transdermally.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

In another embodiment, a pharmaceutical composition comprising a compound disclosed herein, a derivative or analog thereof, including pharmaceutical salt forms and prodrug forms, can be formulated either alone or in combination with one or more additional therapeutic agents, including, but not limited to, antibiotics, antifungal-agents, anti-pruritics, analgesics, and/or antiviral agents, for topical administration. The topical administration, as used herein, include (intra)dermal, conjunctival, intracorneal, intraocular, ophthalmic, auricular, transdermal, nasal, vaginal, uretheral, respiratory, and rectal administration. Such topical formulations are useful in treating or inhibiting infections of the eye, skin, and mucous membranes (e.g., mouth, vagina). Examples of formulations in the market place include topical lotions, creams, soaps, wipes, and the like.

A pharmaceutical composition comprising a compound disclosed herein, a derivative or analog thereof, including pharmaceutical salt forms and prodrug forms, may be formulated in any dosage form that is suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation comprising a compound disclosed herein may also comprise liposomes, micelles, microspheres, nanosystems, and mixtures thereof.

Pharmaceutically acceptable carriers and excipients suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

A pharmaceutical composition comprising a compound disclosed herein, a derivative or analog thereof, including pharmaceutical salt forms and prodrug forms, may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

A pharmaceutical composition comprising a compound disclosed herein, a derivative or analog thereof, including pharmaceutical salt forms and prodrug forms, may be formulated in the forms of ointments, creams, sprays and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

A pharmaceutical composition comprising a compound disclosed herein, a derivative or analog thereof, including pharmaceutical salt forms and prodrug forms, may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions disclosed herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

A pharmaceutical composition comprising a compound disclosed herein, a derivative or analog thereof, including pharmaceutical salt forms and prodrug forms, may be administered ophthalmically in the forms of solutions, suspensions, ointments, emulsions, gel-forming solutions, powders for solutions, gels, ocular inserts, and implants. A pharmaceutical composition comprising a compound disclosed herein, a derivative or analog thereof, including pharmaceutical salt forms and prodrug forms, may be administered intranasally or by inhalation to the respiratory tract. A pharmaceutical composition comprising a compound disclosed herein, a derivative or analog thereof, including pharmaceutical salt forms and prodrug forms, may be formulated in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. A pharmaceutical composition comprising a compound disclosed herein, a derivative or analog thereof, including pharmaceutical salt forms and prodrug forms, may also be formulated as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient disclosed herein, a propellant as solvent; and/or a surfactant, such as sorbitan trioleate, oleic acid, or an oligolactic acid.

A pharmaceutical composition comprising a compound disclosed herein, a derivative or analog thereof, including pharmaceutical salt forms and prodrug forms, may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions disclosed herein; a suitable powder base, such as lactose or starch; and a performance modifier, such as 1-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. A pharmaceutical composition comprising a compound disclosed herein, a derivative or analog thereof, including pharmaceutical salt forms and prodrug forms, for inhaled/intranasal administration may further comprise a suitable flavor, such as menthol and levomenthol, or sweeteners, such as saccharin or saccharin sodium.

A pharmaceutical composition comprising a compound disclosed herein, a derivative or analog thereof, including pharmaceutical salt forms and prodrug forms, for topical administration may be formulated to be immediate release or modified release, including delayed-, sustained-, pulsed-, controlled-, targeted, and programmed release.

A pharmaceutical composition comprising a compound disclosed herein, a derivative or analog thereof, including pharmaceutical salt forms and prodrug forms, may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

A pharmaceutical composition comprising a compound disclosed herein, a derivative or analog thereof, including pharmaceutical salt forms and prodrug forms, may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s). Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

The pharmaceutical composition comprising a compound disclosed herein, a derivative or analog thereof, including pharmaceutical salt forms and prodrug forms, that is formulated in a modified release dosage form may be fabricated using a matrix controlled release device (see, Takada et al in "Encyclopedia of Controlled Drug Delivery," Vol. 2, Mathiowitz ed., Wiley, 1999).

In one embodiment, the pharmaceutical composition comprising a compound disclosed herein, a derivative or analog thereof, including pharmaceutical salt forms and prodrug forms, in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, a pharmaceutical composition comprising a compound disclosed herein, a derivative or analog thereof, including pharmaceutical salt forms and prodrug forms are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

A pharmaceutical composition comprising a compound disclosed herein, a derivative or analog thereof, including pharmaceutical salt forms and prodrug forms, in a modified release dosage form may be prepared by methods known to those skilled in the art, including direct compression, dry or wet granulation followed by compression, melt-granulation followed by compression.

The pharmaceutical composition comprising a compound disclosed herein, a derivative or analog thereof, including pharmaceutical salt forms and prodrug forms, in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s) and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition comprising a compound disclosed herein, a derivative or analog thereof, including pharmaceutical salt forms and prodrug forms, in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In a certain embodiment, a pharmaceutical composition comprising a compound disclosed herein, a derivative or analog thereof, including pharmaceutical salt forms and prodrug forms are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In a particular embodiment, a pharmaceutical composition comprising a compound disclosed herein, a derivative or analog thereof, including pharmaceutical salt forms and prodrug forms are formulated as ESC controlled-release dosage form, which comprises an osmotic membrane that coats a core comprising the active ingredient(s), a hydroxyethyl cellulose, and other pharmaceutically acceptable excipients or carriers.

A pharmaceutical composition comprising a compound disclosed herein, a derivative or analog thereof, including pharmaceutical salt forms and prodrug forms, may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

A pharmaceutical composition comprising a compound disclosed herein, a derivative or analog thereof, including pharmaceutical salt forms and prodrug forms, may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical composition comprising a compound disclosed herein, a derivative or analog thereof, including pharmaceutical salt forms and prodrug forms, may include one or more pharmaceutically acceptable carriers and excipients, including, but not limited to, aqueous vehicles, water-miscible vehicles, non-aqueous vehicles, antibacterial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Preparations for parenteral administration of a pharmaceutical composition comprising a compound disclosed herein, a derivative or analog thereof, including pharmaceutical salt forms and prodrug forms include sterile aqueous or non-aqueous solutions, suspensions, and emulsions. Suitable aqueous vehicles include, but are not limited to, water, saline, physiological saline or phosphate buffered saline (PBS), sodium chloride injection, Ringers injection, isotonic dextrose injection, sterile water injection, dextrose, lactated Ringers injection, alcoholic/aqueous solutions, and emulsions or suspensions. Non-aqueous vehicles include, but are not limited to, injectable organic esters such as ethyl oleate, and fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antibacterials, anti-oxidants, cheating agents, inert gases and the like also can be included.

Suitable antibacterial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

A pharmaceutical composition comprising a compound disclosed herein, a derivative or analog thereof, including pharmaceutical salt forms and prodrug forms may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical composition comprising a compound disclosed herein, a derivative or analog thereof, including pharmaceutical salt forms and prodrug forms are formulated as ready-to-use sterile solutions. In another embodiment, the pharmaceutical composition comprising a compound disclosed herein, a derivative or analog thereof, including pharmaceutical salt forms and prodrug forms are formulated as sterile dry soluble products, including lyophilized powders and hypodermic tablets, to be reconstituted with a vehicle prior to use. In yet another embodiment, the pharmaceutical composition comprising a compound disclosed herein, a derivative or analog thereof, including pharmaceutical salt forms and prodrug forms are formulated as ready-to-use sterile suspensions. In yet another embodiment, the pharmaceutical composition comprising a compound disclosed herein, a derivative or analog thereof, including pharmaceutical salt forms and prodrug forms are formulated as sterile dry insoluble products to be reconstituted with a vehicle prior to use. In still another embodiment, the pharmaceutical composition comprising a compound disclosed herein, a derivative or analog thereof, including pharmaceutical salt forms and prodrug forms are formulated as ready-to-use sterile emulsions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

A pharmaceutical composition comprising a compound disclosed herein, a derivative or analog thereof, including pharmaceutical salt forms and prodrug forms, suitable for injectable use include sterile aqueous solutions (where water soluble) or dispersions and sterile powders for the extemporaneous preparation of sterile injectable solutions or dispersions. In all cases, the pharmaceutical composition comprising a compound disclosed herein, a derivative or analog thereof, including pharmaceutical salt forms and prodrug forms, should be sterile and should be fluid to the extent that easy syringability exists. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating a pharmaceutical composition comprising a compound disclosed herein, a derivative or analog thereof, including pharmaceutical salt forms and prodrug form in the required amount in an appropriate solvent with one or a combination of ingredients enumerated above, as required, followed by filtered sterilization. Generally, dispersions are prepared by incorporating a pharmaceutical composition comprising a compound disclosed herein, a derivative or analog thereof, including pharmaceutical salt forms and prodrug forms, into a sterile vehicle that contains a basic dispersion medium and the required other ingredients from those enumerated above.

A pharmaceutical composition comprising a compound disclosed herein, a derivative or analog thereof, including pharmaceutical salt forms and prodrug forms, can be orally administered, for example, with an inert diluent or an assimilable edible carrier. The pharmaceutical composition comprising a compound disclosed herein, a derivative or analog thereof, including pharmaceutical salt forms and prodrug forms, and other ingredients can also be enclosed in a hard or soft-shell gelatin capsule, compressed into tablets, or incorporated directly into the individual's diet. For oral therapeutic administration, the pharmaceutical composition comprising a compound disclosed herein, a derivative or analog thereof, including pharmaceutical salt forms and prodrug forms, can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed.

A pharmaceutical composition comprising a compound disclosed herein, a derivative or analog thereof, including pharmaceutical salt forms and prodrug forms are disclosed herein, may be formulated as immediate or modified release dosage forms, including delayed-, sustained-, pulsed-, controlled, targeted-, and programmed-release forms.

A pharmaceutical composition comprising a compound disclosed herein, a derivative or analog thereof, including pharmaceutical salt forms and prodrug forms are disclosed herein, may be formulated as a suspension, solid, semi-solid, or thixotropic liquid, for administration as an implanted depot. In one embodiment, the pharmaceutical composition comprising a compound disclosed herein, a derivative or analog thereof, including pharmaceutical salt forms and prodrug forms are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

A therapeutically effective amount can be measured as the amount sufficient to decrease a subject's symptoms (e.g., dermatitis or rash by measuring the frequency of severity of skin sores). Typically, the subject is treated with an amount of a therapeutic composition comprising a compound disclosed herein, a derivative or analog thereof, including pharmaceutical salt forms and prodrug forms, sufficient to reduce a symptom of a disease or disorder by at least 50%, 90% or 100%. Generally, the optimal dosage will depend upon the disorder and factors such as the weight of the subject, the type of bacteria, virus or fungal infection, the weight, sex, and degree of symptoms. Nonetheless, suitable dosages can readily be determined by one skilled in the art. Typically, a suitable dosage is 0.5 to 40 mg/kg body weight, e.g., 1 to 8 mg/kg body weight.

The compounds disclosed herein may also be combined or used in combination with other agents useful in the treatment, prevention, or amelioration of one or more symptoms of various syndromes, disorders, and/or diseases. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein disclosed herein is used contemporaneously with one or more other drugs, a pharmaceutical composition containing such other drugs in addition to the compound disclosed herein may be utilized, but is not required. Accordingly, the pharmaceutical compositions disclosed herein include those that also contain one or more other active ingredients or therapeutic agents (e.g., an inhibitor of TNF, an antibiotic, and the like), in addition to a compound disclosed herein. Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal, antiviral and/or anti-fungal amount. Their effects can also be augmented by co-administration with an inhibitor of flavohemoglobin, (Helmick et al., Imidazole antibiotics inhibit the nitric oxide dioxygenase function of microbial flavohemoglobin. Antimicrob Agents Chemother, 2005, 49(5):1837-43, and Sud et al., Action of antifungal imidazoles on *Staphylococcus aureus*, Antimicrob Agents Chemother, 1982, 22(3):470-4), increasing the efficacy of NO-based *S. aureus* killing by macrophages, and optionally triple combination therapies comprising one squalene synthase inhibitor, one flavohemoglobin (nitric oxide dioxygenase) inhibitor such as an azole (miconazole, econazole, clortrimazole, and ketoconazole) and one antibiotic as described above, may be applied to a patient in need of therapy. In a certain embodiment, a compound disclosed herein can be combined with one or more antibiotics, including, but not limited to, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, clofazimine, cloxacillin, colistin, dalfopristan, demeclocycline, dicloxacillin, dirithromycin, doxycycline, erythromycin, enafloxacin, enviomycin, ertepenem, ethambutol, flucloxacillin, fosfomycin, furazolidone, gatifloxacin, geldanamycin, gentamicin, herbimicin, imipenem, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, oxytetracycline, penicillin, piperacillin, platensimycin, polymixin B, prochlorperazine, prontocil, quinupristine, rifabutin, roxithromycin, spectinomycin, sulfacetamide, sulfamethizole, sulfamethoxazole, teicoplanin, telithromycin, tetracycline, thioacetazone, thioridazine, ticarcillin, tobramycin, trimethoprim, troleandomycin, trovafloxacin, and vancomycin.

In a further embodiment, a compound provided herein can be combined with one or more sepsis treatments known in the art, including, but not limited to, antibiotics, vasopressors, and corticosteroids.

In yet a further embodiment, a compound provided herein can be combined with one or more steroidal drugs known in the art, including, but not limited to, aldosterone, beclometasone, betamethasone, deoxycorticosterone acetate, fludrocortisone acetate, hydrocortisone (cortisol), prednisolone, prednisone, methylprenisolone, dexamethasone, and triamcinolone.

In certain embodiments, a compound disclosed herein can be combined with one or more anti-fungal agents, including, but not limited to, amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

The compounds disclosed herein can also be administered in combination, preferably sequentially, with other classes of compounds, including, but not limited to, antipruritics; anticoagulants, such as bivalirudin; thrombolytics, such as streptokinase; non-steroidal anti-inflammatory agents, such as aspirin; antiplatelet agents, such as clopidogrel; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anti-coagulants, such as warfarin; low molecular weight heparins, such as enoxaparin; Factor VIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; anti-inflammatories; anti-proliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); anti-metabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

The disclosure provides a method for inhibiting a bacterial, viral, parasitic and/or fungal-associated disorder by contacting or administering a therapeutically effective amount of a compound disclosed herein, derivative or analog thereof either alone or in combination with other antimicrobial agents to a subject who has, or is at risk of having, such a disorder. The term "inhibiting" means preventing or ameliorating a sign or symptoms of a syndrome, disorder, and/or disease (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, adult respiratory distress syndrome, shock, rash, and organ failure. Examples of subjects who can be treated in the disclosure include those at risk for, or those suffering from, a toxemia, such as endotoxemia resulting from a gram-negative or gram-positive bacterial infection. Other examples include subjects having dermatitis as well as those having skin infections or injuries subject to infection with gram-positive or gram-negative bacteria, a virus, or a fungus. Examples of candidate subjects include those suffering from infection by *E. coli, Neisseria meningitides*, staphylococci, or pneumococci. Other subjects include those suffering from gunshot wounds, renal or hepatic failure, trauma, burns, immunocompromising infections (e.g., HIV infections), hematopoietic neoplasias, multiple myeloma, Castleman's disease or cardiac myxoma. Those skilled in the art of medicine can readily employ conventional criteria to identify appropriate subjects for treatment in accordance with the disclosure.

The disclosure also provides a method for inhibiting the growth of a bacterium by contacting the bacterium with compound, derivative or analog thereof, including pharmaceutical salt and prodrug forms, with an inhibiting effective amount. The term "contacting" refers to exposing the microbe (e.g., bacterium) to an agent so that the agent can inhibit, kill, or lyse microbe or render it susceptible to oxidative destruction.

Contacting can occur in vivo, for example, by administering the compound, derivative or analog thereof, including pharmaceutical salt and prodrug forms, to a subject afflicted with a bacterial infection or is susceptible to a bacterial infection. In vivo contacting includes both parenteral as well as topical. "Inhibiting" or "inhibiting effective amount" refers to the amount of agent that is sufficient to cause, for example, a bacteriostatic or bactericidal effect. Bacteria that can be affected by the use of a compound, derivative or analog thereof, including pharmaceutical salt and prodrug forms, include both gram-negative and gram-positive bacteria. For example, bacteria that can be affected include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus* anthraces, *Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. The method for inhibiting the growth of bacteria can also include contacting the bacterium with a compound disclosed herein, derivative or analog, including pharmaceutical salt and prodrug forms, thereof in combination with one or more antibiotics.

Fungal organisms may also be affected by a compound disclosed herein, derivative or analog thereof, including pharmaceutical salt and prodrug forms, include for example, *Microsporum canis* and other *Microsporum* sp.; *Trichophyton* sp. such as *T. rubrum*, and *T. mentagrophytes*, yeasts, e.g., *Candida albicans, C. Tropicalis*, or other *Candida* species, *Saccharomyces cerevisiae, Torulopsis glabrata, Epidermophyton floccosum, Malassezia furfur (Pityropsporon orbiculare*, or *P. ovale, Cryptococcus neoformans, Aspergillus fumigatus, Aspergillus nidulans*, and other *Aspergillus* sp., Zygomycetes, e.g., *Rhizopus, Mucor, Paracoccidioides brasiliensis, Blastomyces dermatitides, Histoplasma capsulatum, Coccidioides immitis*, and *Sporothrix schenckii*.

The methods and compositions of the disclosure utilizing Firmocidin compound, derivative or analog thereof are useful as a broad-spectrum antimicrobials suitable for tackling the growing problem of antibiotic-resistant bacteria strains, and for treating and/or preventing outbreaks of infectious diseases, including diseases caused by bioterrorism agents like anthrax, plague, cholera, gastroenteritis, multidrug-resistant tuberculosis (MDR TB).

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound disclosed herein with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art. The invention is further illustrated by the following examples:

EXAMPLES

Initial purification involved 5 steps including three modes of chromatography. High-resolution ES-mass spectrometry analysis predicted the antibiotic component to have a molecular formula of $C_5H_5N_5O$. The chemical shifts obtained by NMR structural analyses were found to correlate to the shifts of adenine-N oxide. Based on the structural anlyses, the compound, firmocidin, did not match any prior known antimicrobial agents. When S. epidermidis was cultured in the presence of ammonium-$^{15}$N chloride, the isotope was incorporated into firmocidin, indicating that firmocidin is produced via de novo synthesis and by the fermentation of culture media. Firmocidin killed 99.75% of group A streptococcus, 99.12% of group B streptococcus and 96.84% of Staphylococcus aureus when used at 60 µg/ml for 3 h. Firmocidin also suppressed growth of methicillin-resistant S. aureus strains. Its antimicrobial activity was stronger in these assays than the antimicrobial, benzoyl peroxide, which is one of the most frequently used active ingredients in topically administered therapeutics. However, firmocidin did not affect the growth of S. epidermidis itself. Firmocidin also did not affect viability of human keratinocytes and sebocytes in culture. Thus, firmocidin shows pathogen-specific activity and low toxicity while maintaining S. epidermidis viability and potentially a normal microbiome. Our data support the hypothesis that S. epidermidis contributes to skin innate immune defense and suggests a novel therapeutic approach to normalize skin bacterial colonization.

Purification of firmocidin. Several S. epidermidis strains were clinically isolated from healthy human skin and screened by radial diffusion antimicrobial assays. Extracts form S. epidermidis strain MO34 were found to have the highest antimicrobial activity. Consequently, S. epidermidis strain MO34 was used for all future studies. S. epidermidis strain MO34 bacteria were cultured in reduced media comprised of 25% tryptic soy broth (Sigma) at 37° C. for 24 hours. The supernatant was then purified from the bacterial cells by filtering the bacterial culture through a 0.2 µm filter. After all liquid from the supernatant was removed in vacuo, the resulting residue was re-suspended in methanol. The supernatant was centrifuged, dried, and then partitioned by adding 90% acetonitrile/10% water. The organic layer was collected and dried under nitrogen gas. The resulting residue was dissolved in 2% acetonitrile/98% water and then loaded onto a $C_{18}$ sep-pak cartridge (log; Waters Inc.). The cartridge was washed with 2% acetonitrile (35 mL), followed by elution with 2% acetonitrile (40 mL). The eluent was dried, and then re-suspended in 100% acetonitrile. The resulting crude product was then purified by using HPLC with a Taskgel $NH_2$-100 column (4.5 mm×150 mm; Tosoh Bioscience) in hydrophilic-interaction (HILIC) mode. The title product was eluted by using a linear gradient of 5-20% water in acetonitrile at a flow rate of 1 mL/min; the eluent was monitored at 270 nm. Fractions 26-31 were lyophilized, reconstituted in PBS and applied on an agar plate inoculated with GAS (NZ131). Fractions purified from the S. epidermidis strain were screened by radial diffusion antimicrobial assays. Clear zones on the agar plates indicate antimicrobial activity of the fractions. It was found that fraction #28, which correlated to a peak on the chromatogram, showed significant antimicrobial activity (see e.g., FIG. 2). When S. epidermidis straine MO34 was cultured in the presence of ammonium-$^{15}$N chloride, the isotope was incorporated into firmocidin, indicating that firmocidin is produced via de novo synthesis and not by fermentation of culture media. Approximately, 7 mg of the antibiotic component from fraction #28 was purified from culture supernatant (6 L) for use in future studies.

Figure 4:
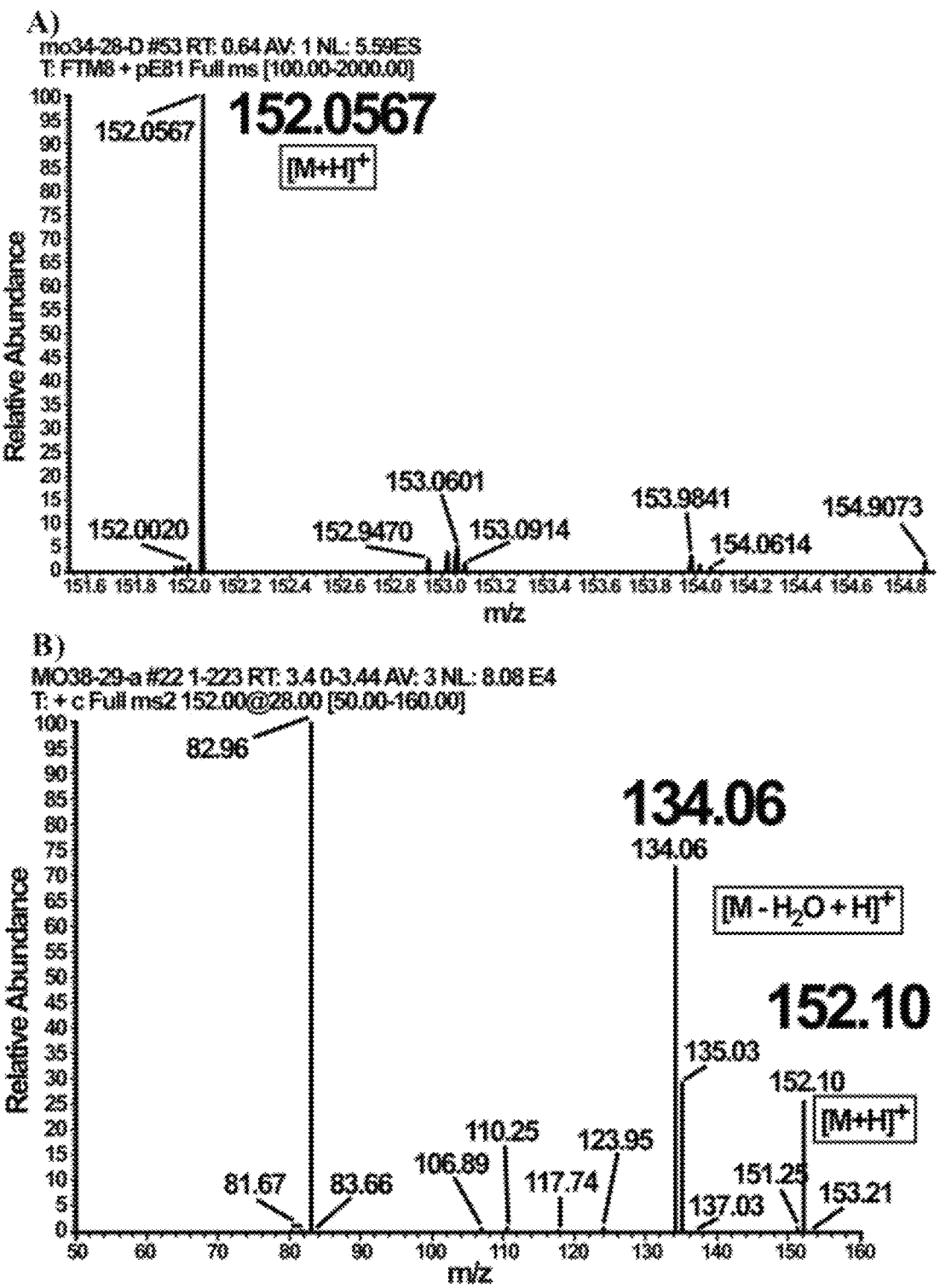
FIG. 4A-B presents (A) a high-resolution ESI-FT-MS spectrum verifying that firmocidin has a predicted molecular mass of 152.0567; and (B) ESI positive ion mode MS/MS analysis on the m/z peak of 152.0567.
Figure 5:
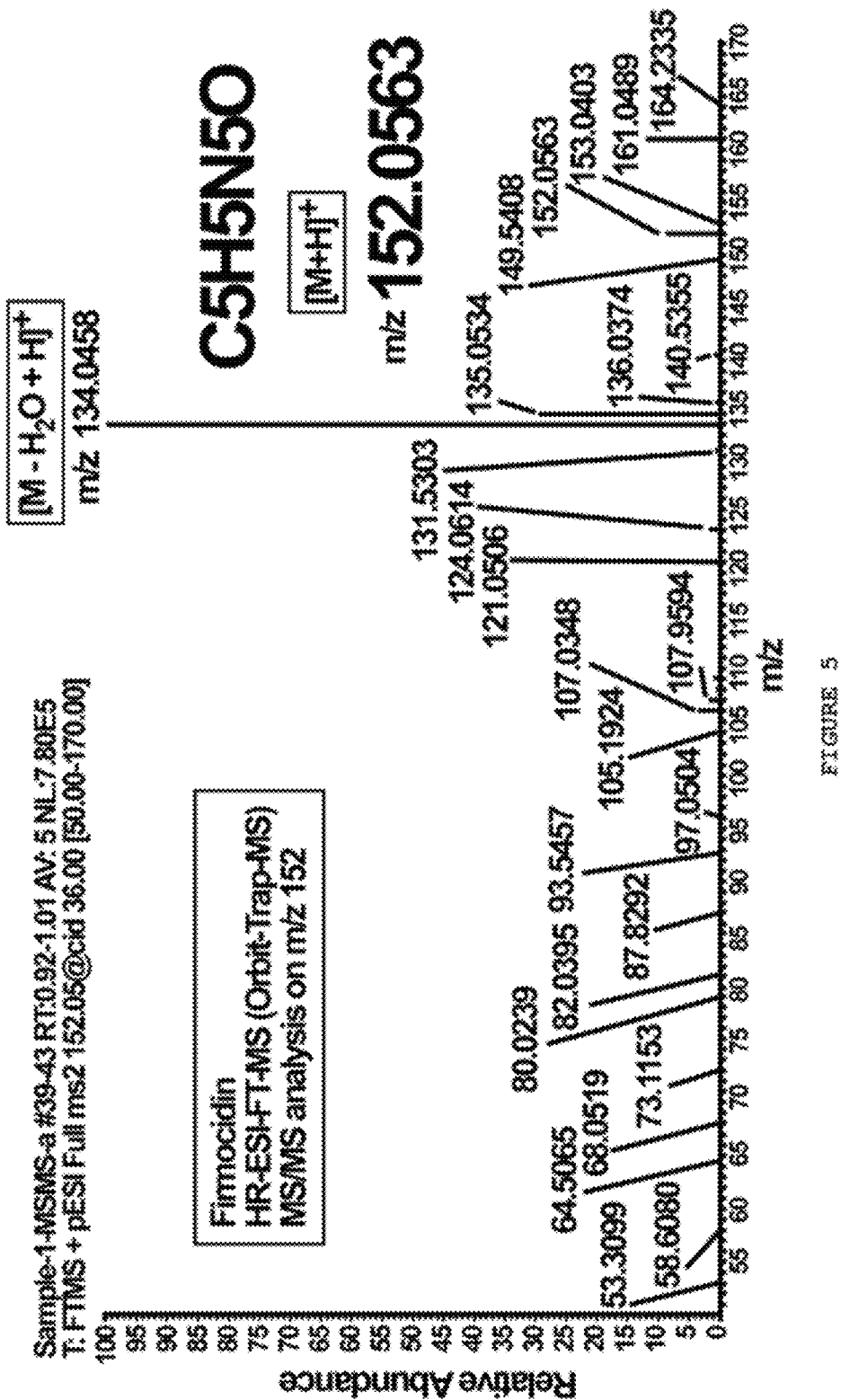
FIG. 5 presents a side by side comparison of the high-resolution HR-ESI-FT-MS spectra for firmocidin and guanine. The difference and similarities in the major electron impact fragmentation of firmocidin versus guanine is readily apparent.
Figure 5:
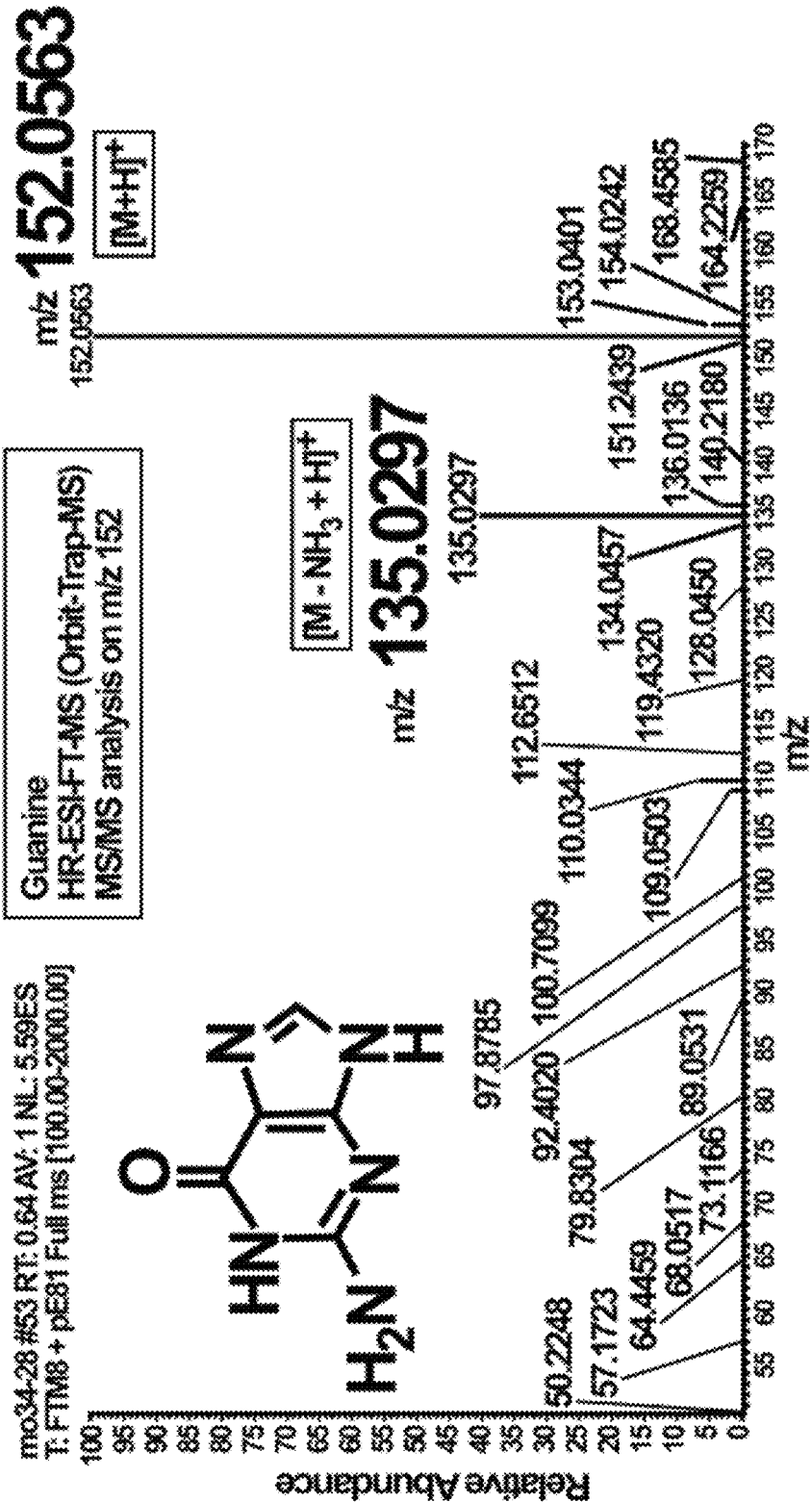
Figure 6:
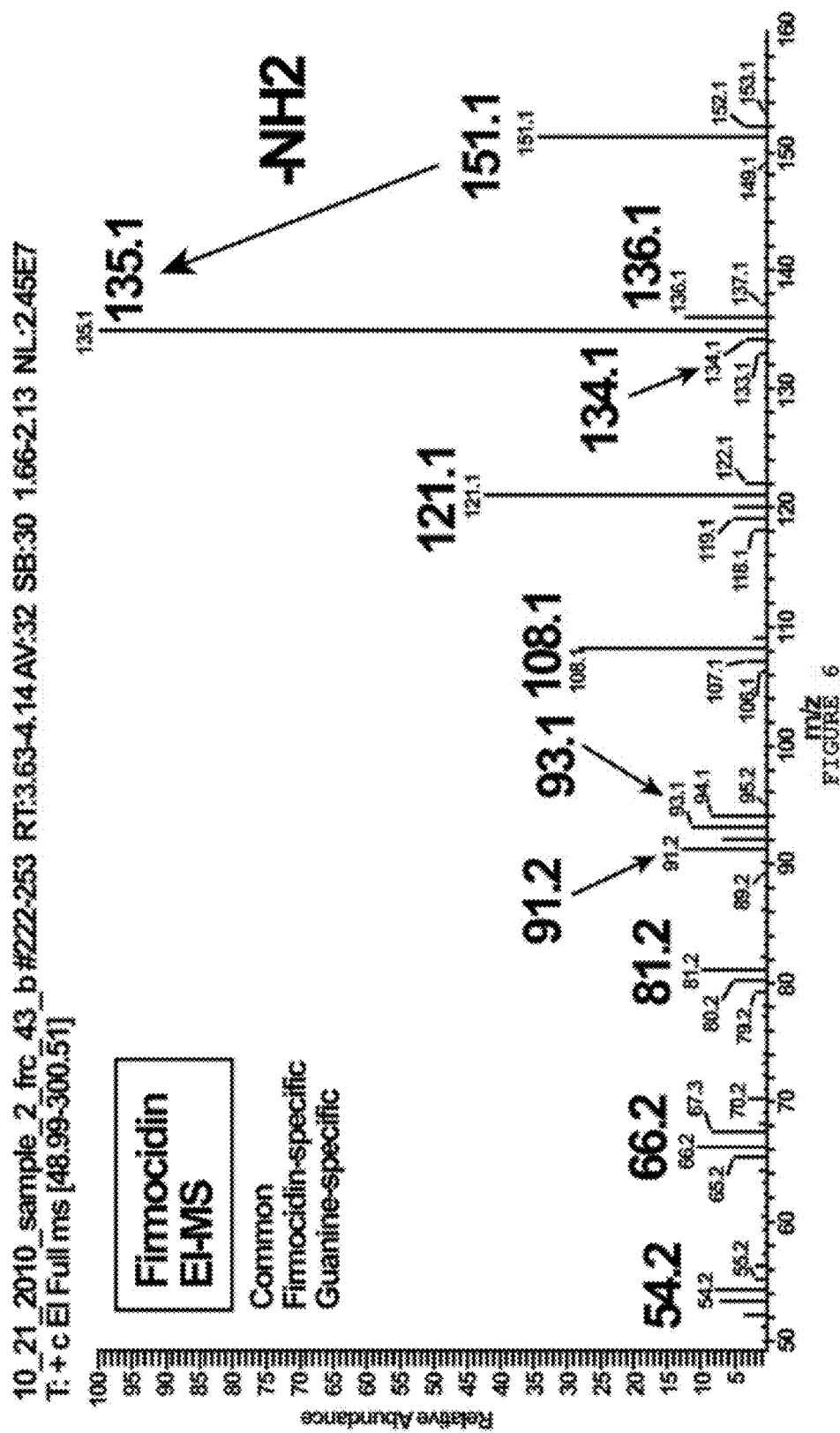
FIG. 6 presents EI-MS spectra showing the difference between firmocidin and guanine. The mass spectra show that firmocidin has fragment peaks that are present and not present in the guanine chromatogram.
Figure 6:
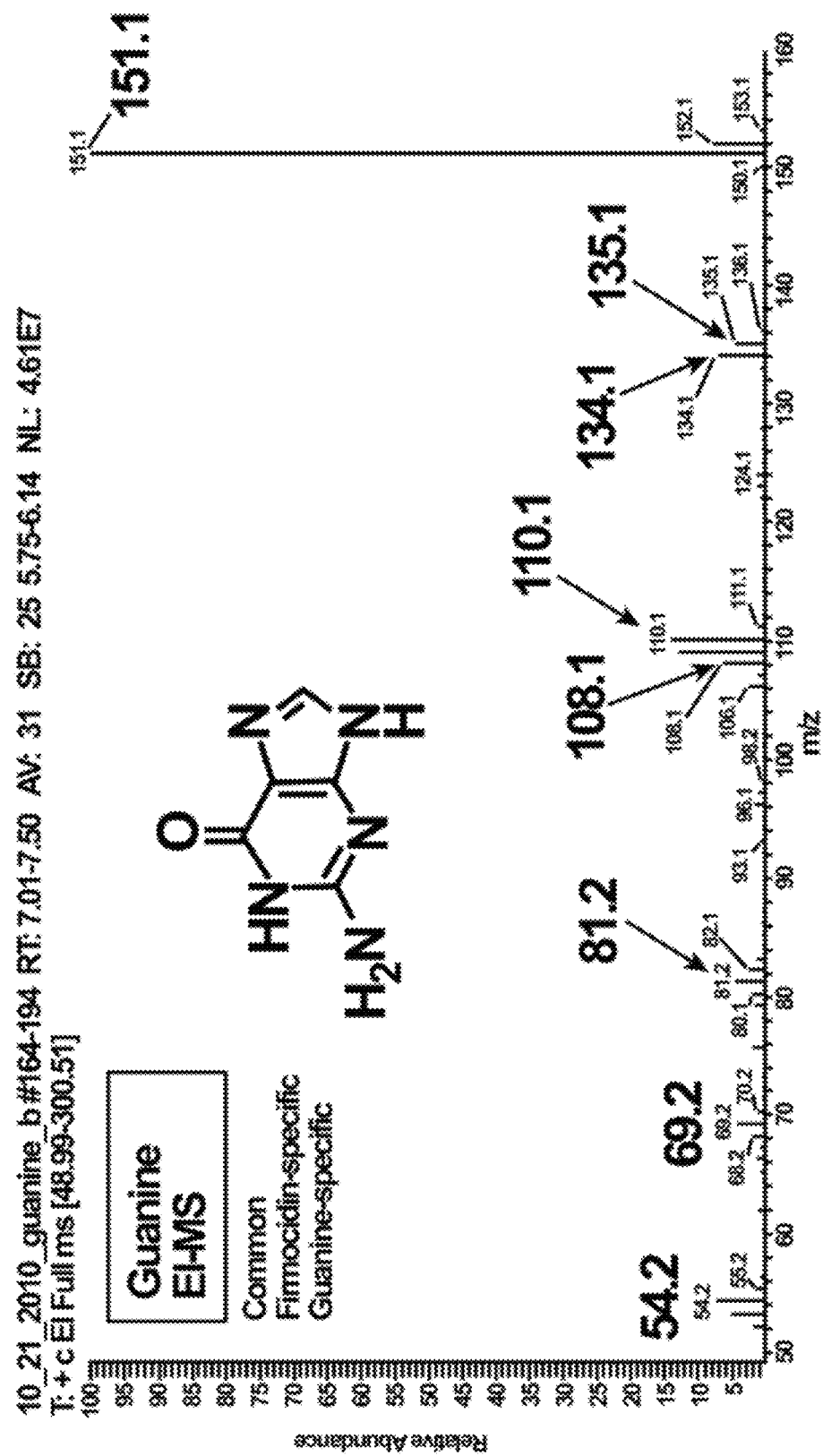
Figure 7:
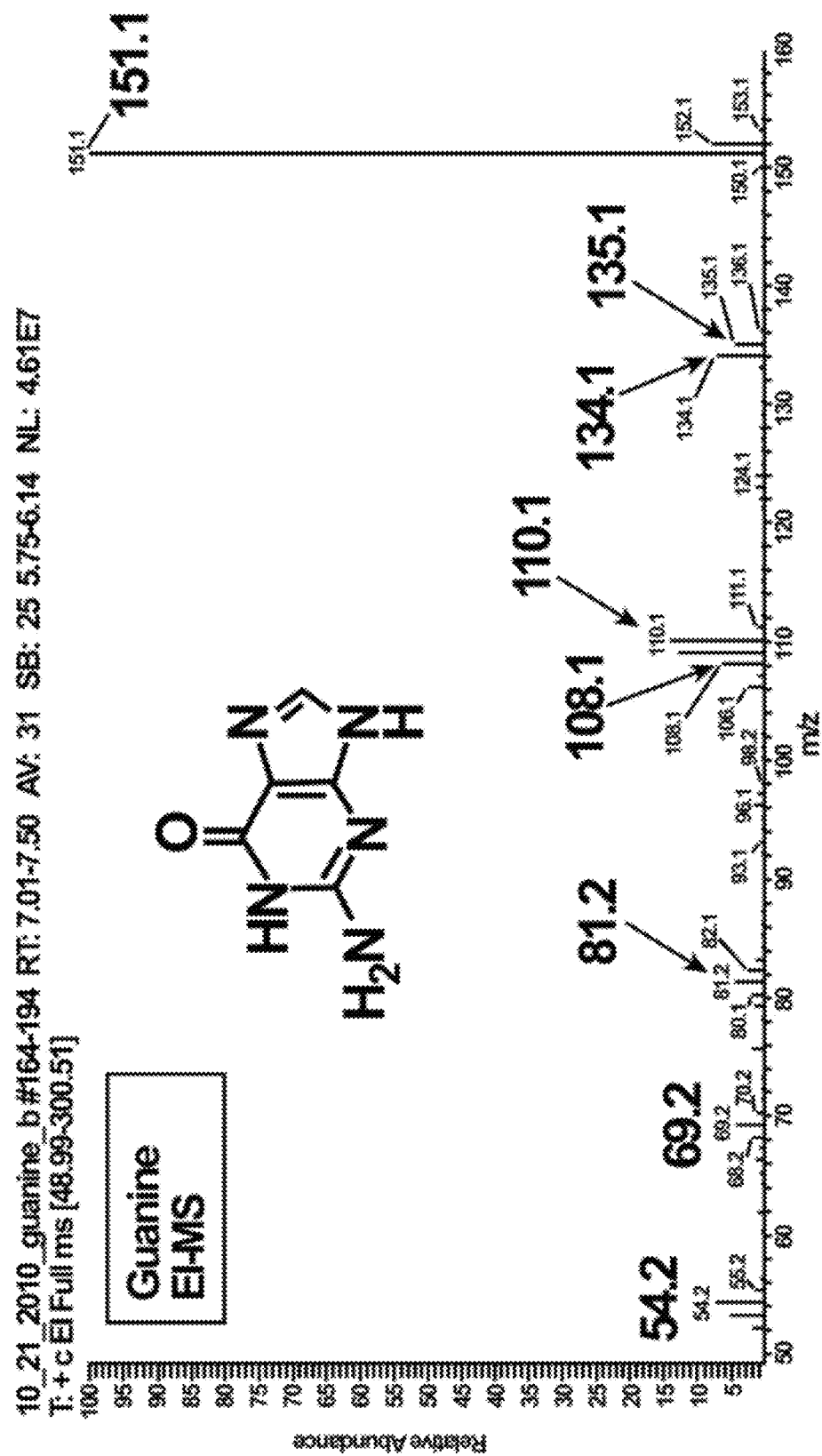
FIG. 7 presents mass spectrum and major electron impact fragmentation of guanine. Wherein, fragment peaks at 69.2 and 110.1 of the guanine mass spectrum are not present in the mass spectrum for firmocidin.
Figure 8:
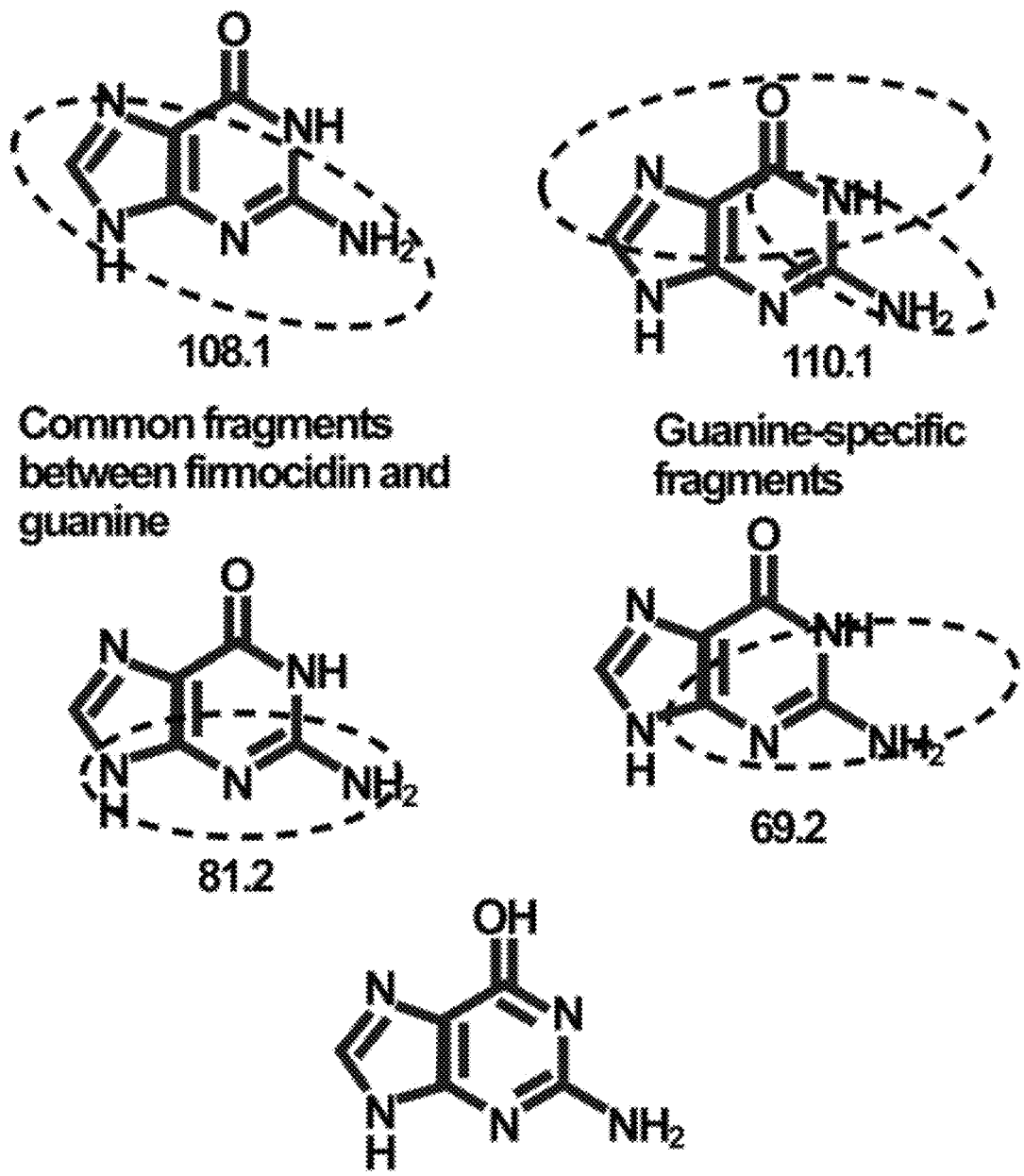
FIG. 8 presents structural models demonstrating select electron impact fragments that are common to both fimocidin and guanine and electron impact fragments that are guanine specific. Atoms encompassed in the dashed ovals represent the major fragment observed along with the predicted mass of the fragment. The guanine specific fragment m/z peak at 110.1 is a singular fragment containing the atoms resulting from the combination of the two dashed ovals.

Mass Spectroscopy. High-resolution ES-MS analysis gave the molecular formula $C_5H_5N_5O$ (calculated exact mass for $[M+H]^+$=152.0567, observed mass=152.0567) (see e.g., FIG. 3-4). In addition, ESI positive ion mode MS/MS analysis on the peak of 152.0567 predicts that firmocidin has at least one hydroxyl group (see e.g., FIG. 4B). The fragmentation profile of firmocidin did not match 6-hydroxyamino purine or guanine in electron-impact mass spectrometry experiments (see e.g., FIGS. 5-8). While data produced from mass spectrometry are typically reproducible and consistent, the data produced, such as the m/z ion fragment peaks, can be affected by sample preparation, temperature, quality of calibration, differences in devices utilized, etc. Accordingly, the data presented in FIGS. 3-8 can potentially vary up to 10 milli mass units.

$^1$H and $^{12}$C NMR spectrum. 1H NMR spectra were recorded at 20° C. at 500 MHz with a Bruker Avance 750

NMR instrument spectrometer. HPLC-purified firmocidin was dissolved in deuterium oxide (100%) (Cambridge isotope Inc.) at 2 mg/mL. The $^1$H spectrum of firmocidin has nuclear shifts at 8.0-8.5 ppm suggesting that firmocidin has a benzene ring (see e.g., FIG. 10). In addition, the chemical shifts from the 2D-NMR studies indicate that firmocidin is a novel antimicrobial agent, in that the chemical shifts did not match any previously characterized antimicrobial agent (see e.g., FIGS. 9-10). The chemical shifts obtained by NMR structural analyses, however, correlated to the shifts seen with an adenine-N oxide. While data produced from NMR are generally reproducible and consistent, the data produced can be affected by sample preparation, temperature, differences in devices utilized, etc. Accordingly, the data generated, such as the ppm peaks, presented in FIGS. 9-10 can vary by plus or minus one ppm.

In vitro antibacterial studies. Purified firmocidin was prepared at minimal bactericidal concentrations. The in-vitro time-bacteria kill curves were then determined in the presence of carbonate. But since Group A *Streptococcus* (GAS) will not grow in media containing carbonate (Dorschner et al., 2006), the in-vitro time-GAS kill curves were determined in media (25% Todd-Hewitt Broth, 75% of 1× Dulbecco's phosphate-buffered saline) that did not contain carbonate. As a control for the GAS in-vitro time-bacteria kill curve, GAS and *S. epidermidis* were grown in the same medium.

Purified firmocidin suppresses growth of GAS, group B *streptococcus* (GBS), methicillin-sensitive *S. aureus* and MRSA, but not *S. epidermidis* (see e.g., FIG. 12) and Gram negative bacteria. Its antimicrobial activity was stronger than benzoyl peroxide (BPO), which is an active ingredient in topically applied medications to treat various conditions, including e.g. acne vulgaris (see e.g., FIG. 12). Furthermore, the in-vitro time-bacteria kill curves demonstrate that firmocidin exhibits bactericidal activity against GAS and bacteristatic activity against GBS and *S. aureus* (see FIG. 13), but not against *S. epidermidis*. Firmocidin killed 99.75% of group A *streptococcus*, 99.12% of group B *streptococcus* and 96.84% of *Staphylococcus aureus* when used at 60 µg/ml for 3 h. Firmocidin also suppressed growth of methicillin-resistant *S. aureus* strains. It would be expected that firmocidin would have similar antimicrobial activity against other pathogens which have not been tested. Such pathogens, including but not limited to, *Streptococcus* sp. (viridans group), *S. bovis*, *Streptococcus* (anaerobic species), *Streptococcus pneumoniae*, and *Enterococcus* sp.; Gram-negative cocci such as, for example, *Neisseria gonorrhoeae*, *Neisseria meningitidis*, and *Branhamella catarrhalis*; Gram-positive bacilli such as *Bacillus anthraces, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia, Campylobacter jejuni, Microsporum canis* and other *Microsporum* sp.; *Trichophyton* sp. such as *T. rubrum*, and *T. mentagrophytes*, yeasts, e.g., *Candida albicans*, *C. Tropicalis*, or other *Candida* species, *Saccharomyces cerevisiae, Torulopsis glabrata, Epidermophyton floccosum, Malassezia furfur* (*Pityropsporon orbiculare*, or *P. ovale, Cryptococcus neoformans, Aspergillus fumigatus, Aspergillus nidulans*, and other *Aspergillus* sp., Zygomycetes, e.g., *Rhizopus, Mucor, Paracoccidioides brasiliensis, Blastomyces dermatitides, Histoplasma capsulatum, Coccidioides immitis*, and *Sporothrix schenckii*, can be tested by using the methods provided in this disclosure, or by making obvious variations thereof, including using pathogen specific growth media, pathogen specific growth conditions, etc. Such experiments would be considered routine to one in the skill in the art, in that they are commonly performed and there is extensive documentation with respect to the proper growth conditions for specific pathogenic organisms.

Cytotoxic effect of firmocidin. The immortalized human HaCaT keratinocytes and SZ95 sebocytes were grown to 75% confluence (1×10$^5$ cell/well) and were incubated with various concentrations of firmocidin for 24 hours. As a background, Triton X-100 (0.1% (v/v)) was added to achieve 0% cell viability. After incubation, cell viabilities were determined with a cell viability assay kit (Promega) according to the instruction provided.

Figure 14:
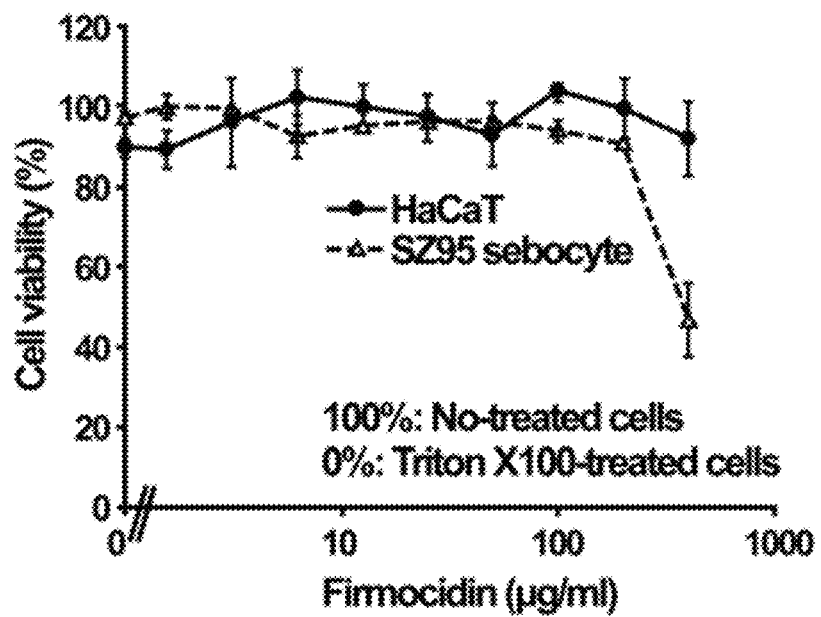
FIG. 14 presents data demonstrating that firmocidin does not have a deleterious effect on the cell viability of human keratinocytes and sebocytes. The immortalized human HaCaT keratinocytes and SZ95 sebocytes ($1 \times 10^5$ cells/well) were incubated with indicated concentrations of firmocidin for 24 hr at 37° C. As a background, Triton X-100 (0.1% (v/v)) was added to achieve 0% cell viability. After incubation, cell viabilities were determined with a MTT assay.

The cell viability studies indicate that firmocidin is not cytotoxic to human keratinocytes and sebocytes (see FIG. 14). The data suggests that firmocidin is safe to use on subjects. Thus, firmocidin is pathogen-specific, and a safe antimicrobial therapy for infections caused by GAS, GBS and *S. aureus*. Furthermore, additional routine experiments may be performed using the methods provided herein, to perform in vitro cell viability studies with other cell lines.

In vivo Studies in a Murine Model. ED50 evaluations are carried out in CF1 female mice injected intraperitoneally with sufficient bacteria to kill 100% of the untreated animals for all methicillin-sensitive and methicillin-resistant *S. aureus* strains. C3H/HeN female mice are utilized in the tests for GAS and GBS studies. Thawed bacterial cultures are suspended in BHI broth which contained 4-8% dried Brewer's yeast (w/v). The infecting inoculum (0.2 mL) is adjusted to yield ca. 100 times the 50% lethal dose (LD50). Concurrently with each trial, the challenge LD50 is validated by inoculating untreated animals with log dilutions of the bacteria. Five dosage levels representing a 5 log dilution range are employed per determination with 10 mice utilized at each level. A mortality rate of 90-100% is produced in all groups of untreated mice with the 100×LD50 challenge inoculum. Test compounds are formulated in water or saline, with gentle heating at higher concentrations, and administered orally or subcutaneously at 1 and 5 hours post-infection. At least five dosage levels of firmocidin utilizing serial 2-fold dilutions are employed for each ED50 determination. One treatment group of six mice is used for each firmocidin dosage level. Deaths in each group following infection and treatment are monitored daily for at least 6 days. Following this observation period, cumulative mortality figures are used to calculate by probit analysis the amount of drug in mg of drug/kg of body Antimicrobial peptides serve as a first line of innate immune defense against invading organisms such as bacteria and viruses. The disclosure demonstrates that antibiotics are produced by a normal microbial resident of human skin, *Staphylococcus epidermidis*, which act as an antimicrobial shield and contribute to normal defense at the epidermal interface. An agent was obtained with antimicrobial activity from culture supernatant of *S. epidermis* MO34, a strain isolated from healthy human skin surface. According to the NMR structure analysis, the component was a novel antibiotic of which chemical formula was $C_5H_5N_5O$ referred to herein as firmocidin. Firmocidin exhibited bactericidal activity against group A streptococcus and bacteriostatic activity against group B streptococcus and *Staphylococcus aureus*. Most notably, firmocidin suppresses growth of methicillin-resistant *S. aureus* (MRSA), a strain that is highly resistant to some antibiotics. However, firmocidin does not affect the growth of *S. epidermidis* which contributes normal defense at the skin epithelium. Firmocidin also did not adversely affect the viability of human keratinocytes and sebocytes. In addition, firmocidin is isolated from a microorganism residing in the normal skin microflora, suggesting low toxicity to the host. Thus, firmocidin may have potential to be safely used as a pathogen-specific antibiotic therapy for skin infections.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a dermatological disease or disorder, comprising contacting a subject having a dermatological disease or disorder with an effective amount of an antimicrobial composition formulated for topical administration, wherein the antimicrobial composition comprises a supernatant of a cultured *Staphylococcus epidermidis* strain capable of producing a firmocidin compound, wherein the cultured *Staphylococcus epidermidis* strain capable of producing the firmocidin compound is *Staphylococcus epidermidis* strain MO34, wherein the antimicrobial composition is capable of inhibiting a skin pathogen associated with the dermatological disease or disorder, and wherein the contacting comprises topical administration.

2. The method of claim 1, wherein the antimicrobial composition is in a suspension, a solution, an emulsion, a gel, a liquid form, or a semisolid form.

3. The method of claim 1, wherein the antimicrobial composition is a lotion, a cream, a soap, a wipe, or any combination thereof.

4. The method of claim 1, wherein the antimicrobial composition is an emulsion, a solution, a suspension, a gel, a hydrogel, an ointment, a dusting powder, a dressing, an elixir, a tincture, a paste, a foam, a film, an aerosol, an irrigation, a spray, a suppository, a bandage, a dermal patch, or any combination thereof.

5. The method of claim 1, wherein the dermatological disease or disorder comprises one or more of wounds, diabetic ulcers, acne, rosacea, atopic dermatitis, pyodermas, and burn wounds.

6. The method of claim 1, wherein the skin pathogen comprises *Staphylococcus aureus, Streptococcus pyogenes, Streptococcus viridans* group, *Streptococcus agalactiae, S. bovis, Streptococcus, Streptococcus pneumoniae, Enterococcus* sp., Gram-negative cocci, *Neisseria gonorrhoeae, Neisseria meningitidis, Branhamella catarrhalis*, Gram-positive bacilli, *P. acnes Corynebacterium diphtheria, Corynebacterium* species, *Listeria monocytogenes, Clostridium tetani, Clostridium difficile, Escherichia coli, Enterobacter* species, *Proteus mirablis, Proteus* sp., *Pseudomonas aeruginosa, Klebsiella pneumoniae, Salmonella, Shigella, Serratia, Campylobacter jejuni, Microsporum* sp., *Trichophyton* sp., *T. rubrum, T. mentagrophytes, Candida albicans, C. Tropicalis, Candida* sp., *Saccharomyces cerevisiae, Torulopsis glabrata, Epidermophyton floccosum, Malassezia furfur, Pityropsporon orbiculare, P. ovale, Cryptococcus neoformans, Aspergillus fumigatus, Aspergillus nidulans, Aspergillus* sp., Zygomycetes, *Rhizopus* sp., *Mucor* sp., *Paracoccidioides brasiliensis, Blastomyces dermatitides, Histoplasma capsulatum, Coccidioides immitis, Sporothrix schenckii*, or any combination thereof.

7. The method of claim 1, wherein the supernatant is derived from the cultured *Staphylococcus epidermidis* strain capable of producing the firmocidin compound by filtration, and wherein the supernatant is dried under vacuum.

8. The method of claim 1, wherein the firmocidin compound inhibits the growth of Group A streptococcus (GAS), Group B streptococcus (GBS), and *S. aureus* in a protease-resistant manner, wherein the firmocidin compound does not inhibit the growth of *S. epidermidis*, and wherein the firmocidin compound is not cytotoxic to HaCaT keratinocyte cells or SZ95 sebocyte cells at concentrations of 100 ug/ml or less.

9. The method of claim 1, wherein the skin pathogen comprises a Group A, Group B Streptococcus, or a yeast.

10. The method of claim 6, wherein the Gram-positive bacilli is *Bacillus anthracis* or *Bacillus subtilis*.

11. A composition comprising a supernatant of a cultured *Staphylococcus epidermidis* strain capable of producing the firmocidin compound, wherein the cultured *Staphylococcus epidermidis* strain capable of producing the firmocidin compound is *Staphylococcus epidermidis* strain MO34, wherein the composition is capable of inhibiting a skin pathogen associated with the dermatological disease or disorder, and wherein the composition is formulated for topical administration.

12. The composition of claim 11, wherein the supernatant is present in a liposome, a micelle, a microsphere, a nanosystem, or any combination thereof.

13. The composition of claim 11, wherein the supernatant is present in a lotion, a cream, a soap, a wipe, or any combination thereof.

14. The composition of claim 11, wherein the supernatant is present in an emulsion, a solution, a suspension, a gel, a hydrogel, an ointment, a dusting powder, a dressing, an elixir, a tincture, a paste, a foam, a film, an aerosol, an irrigation, a spray, a suppository, a bandage, a dermal patch, or any combination thereof.

15. The composition of claim 11, wherein the supernatant is derived from the cultured *Staphylococcus epidermidis* strain capable of producing the firmocidin compound by filtration.

16. The composition of claim 15, wherein said filtration comprises utilizing a filter with a 3 kilodalton molecular weight cutoff.

17. The composition of claim 16, wherein said filtration comprises utilizing a 0.2 um filter.

18. The composition of claim 11, wherein the supernatant is dried under vacuum.

19. The composition of claim 11, wherein the firmocidin compound inhibits the growth of Group A streptococcus (GAS), Group B streptococcus (GBS), and *S. aureus* in a protease-resistant manner.

20. The composition of claim 11, wherein the skin pathogen comprises *Staphylococcus aureus, Streptococcus pyogenes, Streptococcus viridans, Streptococcus agalactiae, S. bovis, Streptococcus, Streptococcus pneumoniae, Enterococcus* sp., Gram-negative cocci, *Neisseria gonorrhoeae, Neisseria meningitidis, Branhamella catarrhalis*, Gram-positive bacilli, *P. acnes Corynebacterium diphtheria, Corynebacterium* species, *Listeria monocytogenes, Clostridium tetani, Clostridium difficile, Escherichia coli, Enterobacter* species, *Proteus mirablis, Proteus* sp., *Pseudomonas aeruginosa, Klebsiella pneumoniae, Salmonella, Shigella, Serratia, Campylobacter jejuni, Microsporum* sp., *Trichophyton* sp., *T. rubrum, T. mentagrophytes, Candida albicans, C. Tropicalis, Candida* sp., *Saccharomyces cerevisiae, Torulopsis glabrata, Epidermophyton floccosum, Malassezia furfur, Pityropsporon orbiculare, P. ovale, Cryptococcus neoformans, Aspergillus fumigatus, Aspergillus nidulans, Aspergillus* sp., Zygomycetes, *Rhizopus* sp., *Mucor* sp., *Paracoccidioides brasiliensis, Blasto-*

*myces dermatitides, Histoplasma capsulatum, Coccidioides immitis, Sporothrix schenckii*, or any combination thereof.

21. The composition of claim 11, wherein the skin pathogen comprises a Group A, Group B Streptococcus, or a yeast.

22. The composition of claim 20, wherein the Gram-positive b